(12) United States Patent
Gregori et al.

(10) Patent No.: US 7,214,320 B1
(45) Date of Patent: *May 8, 2007

(54) SYSTEMS AND METHODS FOR HIGH THROUGHPUT SAMPLE ANALYSIS

(75) Inventors: Matthew M. Gregori, Pasadena, CA (US); Joseph F. Covington, San Gabriel, CA (US); Steven E. Hobbs, West Hills, CA (US)

(73) Assignee: Nanostream, Inc., Pasadena, CA (US)

( * ) Notice: Subject to any disclaimer, the term of this patent is extended or adjusted under 35 U.S.C. 154(b) by 188 days.

This patent is subject to a terminal disclaimer.

(21) Appl. No.: 10/979,946

(22) Filed: Nov. 1, 2004

Related U.S. Application Data

(63) Continuation-in-part of application No. 10/951,255, filed on Sep. 25, 2004, and a continuation-in-part of application No. 10/637,234, filed on Aug. 8, 2003, now Pat. No. 6,812,458.

(60) Provisional application No. 60/506,452, filed on Sep. 26, 2003, provisional application No. 60/401,912, filed on Aug. 8, 2002.

(51) Int. Cl.
*B01D 15/08* (2006.01)

(52) U.S. Cl. .................. 210/656; 210/143; 210/198.2; 422/70; 422/100; 73/61.52; 73/61.56; 73/61.58

(58) Field of Classification Search ............... 210/635, 210/656, 659, 143, 198.2, 502.1; 422/70, 422/100; 73/61.52, 61.56, 61.58
See application file for complete search history.

(56) References Cited

U.S. PATENT DOCUMENTS

| | | |
|---|---|---|
| 5,872,010 A | 2/1999 | Karger et al. |
| 6,054,047 A | 4/2000 | Hindsgaul et al. |
| 6,066,848 A | 5/2000 | Kassel et al. |
| 6,264,892 B1 | 7/2001 | Kaltenbach et al. |

(Continued)

FOREIGN PATENT DOCUMENTS

WO    WO-97/04297 A1    2/1997

(Continued)

OTHER PUBLICATIONS

Abian, J., The coupling of gas and liquid chromatography with mass spectrometry, J. Mass Spect., Mar. 1999, pp. 157-168, vol. 34, No. 3.

(Continued)

*Primary Examiner*—Ernest G. Therkorn
(74) *Attorney, Agent, or Firm*—Vincent K. Gustafson; Intellectual Property Technology Law

(57) ABSTRACT

Systems and methods for analyzing a plurality of samples in parallel include a plurality of liquid phase separation regions, a plurality of microfluidic storage regions, and a common mass spectrometer. Samples are separated in parallel in the separation regions to yield a plurality of output streams that are stored in the storage regions. The contents of each storage region, or at least a representative portion thereof, are sequentially discharged, ionized, and directed to the inlet of a mass spectrometer. In this manner, multiple separations are conducted in parallel with outputs provided serially to a common mass spectrometer without any loss of data. Microfluidic storage regions minimize diffusion between bands of separated samples. Portions of separated samples may be directed to fraction collectors.

32 Claims, 12 Drawing Sheets

U.S. PATENT DOCUMENTS

| | | |
|---|---|---|
| 6,318,157 B1 | 11/2001 | Corso et al. |
| 6,410,915 B1 | 6/2002 | Bateman et al. |
| 6,436,292 B1 | 8/2002 | Petro |
| 6,481,453 B1 * | 11/2002 | O'Connor et al. ........ 137/15.04 |
| 6,508,938 B2 | 1/2003 | Maiefski et al. |
| 6,541,768 B2 | 4/2003 | Andrien, Jr. et al. |
| 6,621,075 B2 | 9/2003 | Hindsgaul et al. |
| 6,632,404 B1 | 10/2003 | Freitag et al. |
| 6,641,783 B1 | 11/2003 | Pidgeon et al. |
| 6,649,908 B2 | 11/2003 | Apffel, Jr. et al. |
| 6,656,739 B2 | 12/2003 | Hindsgaul et al. |
| 6,762,406 B2 | 7/2004 | Cooks et al. |
| 6,812,030 B2 | 11/2004 | Ozbal et al. |
| 6,812,458 B2 * | 11/2004 | Gregori et al. ............. 250/288 |
| 6,855,258 B2 | 2/2005 | Petro et al. |
| 6,910,503 B2 | 6/2005 | Schick et al. |
| 6,936,167 B2 * | 8/2005 | Hobbs et al. ............ 210/198.2 |
| 6,976,384 B2 * | 12/2005 | Hobbs et al. .............. 73/61.58 |
| 2002/0017484 A1 | 2/2002 | Dourdeville ............. 210/198.2 |
| 2002/0068366 A1 | 6/2002 | LaDine, et al. |
| 2002/0185184 A1 * | 12/2002 | O'Connor et al. .......... 137/822 |
| 2002/0187560 A1 * | 12/2002 | Pezzuto et al. ............. 436/180 |
| 2002/0189947 A1 | 12/2002 | Paul, et al. |
| 2003/0136904 A1 | 7/2003 | Mukaibatake |
| 2003/0162304 A1 | 8/2003 | Dority et al. |
| 2004/0026617 A1 * | 2/2004 | Gregori et al. ............. 250/288 |

FOREIGN PATENT DOCUMENTS

| | | |
|---|---|---|
| WO | WO-9809315 A1 | 3/1998 |
| WO | WO-00/41214 A1 | 7/2000 |
| WO | WO-00/64557 A1 | 11/2000 |
| WO | WO-02/30486 A2 | 4/2002 |
| WO | WO-02/44684 A2 | 6/2002 |

OTHER PUBLICATIONS

Dunn, John A., et al., A parallel LC/MS/MS system for the high throughput quantification of clinical trial samples. A validation study, waters Micromass Application Note, Oct. 2002, Publisher: Waters Micromass Technologies.

Figeys, Daniel, et al., An Integrated Microfluidics-Tandem Mass Spectrometry System for Automated Protein Analysis, Anal. Chem., Sep. 15, 1998, pp. 3728-3734, vol. 70, No. 18.

Janiszewski, John S., et al., A High-Capacity LC/MS System for the Bioanalysis of Samples Generated from Plate-Based Metabolic Screening, Anal. Chem:, Apr. 1, 2001, pp. 1459-1501, vol. 73, No. 7.

Jiang, Yun, et al., Intergrated Plastic Microfludic Devices with ESI-MS for Drug Screening and Residue Analysis , Anal. Chem., May 1, 2001, pp. 2048-2053, vol. 73, No. 9.

Kameoka, Jun, et al., A Polymeric Microfludic Chip for CE/MS Determination of Small Molecules, Anal. Chem., May 1, 2001, pp. 1935-1941, vol. 73, No. 9.

Liu, H., et al., A 96-Channel Microdevice for High Throughput Electrospray Ionization Mass Spectrometry (ESI/MS), Web document published at: http://www.geocities.com/ResearchTriangle/Lab/4688/ht-ms.html, Jun. 9, 1998.

Lin, Yuehe, et al., Microfluidic devices on polymer substrates for bioanalytical applications, Web document published at: http://www.pnl.gov/microcats/aboutus/publications/microchemical/Microtechpresentation.pdf, 1999.

Little, David, et al., A prallel LC-MS/MS system for high throughput quantification in drug discovery, Micromass Application Note 248, May 2000, Publisher: Micromass Technologies.

Misharin, Alexander S., et al., High-Throughput Mass Spectrometer Using Atmospheric Pressure Ionization and a Cylindrical Ion Trap Array , Anal. Chem., Jan. 15, 2005, pp. 459-470, vol. 77, No. 2.

Moore, Roger E., et al., A Microscale Electrospray Interface Incorporating a Monolithic, Poly(styrene-divinylbenzene) Support for On-Line Liquid, Anal. Chem., Dec. 1, 1998, pp. 4879-4884, vol. 70, No. 23.

Multi-Paraellel-HPLC, Published on the web at http://www.sepiatec.com/download/phplc.pdf, Publisher: SEPIAtec GmbH, Published in : Berlin Germany.

HPLC: Micro LC/MS analysis of biological samples, Web publication; http://www.sge.com, Apr. 1, 1998.

Van Pelt, Colleen K., et al., A Four-Column Parallel Chromatography System for Isocratic or Gradient LC/MS Analyses, Anal. Chem., Feb. 1, 2001, pp. 582-588, vol. 73, No. 3.

Wachs, Timothy, et al., Electrospray Device for Coupling Microscale Separations and Other Miniaturized Devices with Electrospray Mass . . . , Anal. Chem., Feb. 1 , 2001, pp. 632-638, vol. 73, No. 3.

Wagner, Knut, et al., An Automated On-Line Multidimensional HPLC System for Protein and Peptide Mapping with Integrated Sample Preparation, Anal. Chem., Feb. 15, 2002, pp. 809-820, vol. 74, No. 4.

Xu, Rongda, et al., Application of parallel liquid chromatography/mass spectrometry for high throughput microsomal stablility screening of . . . , J. Am. Soc. Mass Spectrom., Feb. 2002, pp. 155-165, vol. 13, No. 2.

Xu, Rongda, et al., High-Throughput Mass-Directed Parallel Purification Incorporating a Multiplexed Single Quadrupole Mass Spectrometer, Anal. Chem., Jul. 1, 2002, pp. 3055-3062, vol. 74, No. 13.

Yang, Liyu, et al., Evaluation of a Four-Channel Multiplexed Electrospray Triple Quadrupole Mass Spectrometer for the Simultaneous . . . , Anal. Chem., Apr. 15, 2001, pp. 1740-1747, vol, 73, No. 8.

Zhang, B., et al., Microfabricated Devices for Capillary Electrophoresis-Electrospray Mass Spectrometry , Anal. Chem., Aug. 1, 1999, pp. 3258-3264, vol. 71, No. 15.

Zweigenbaum, Jerry et al., High-Throughput Bioanalytical LC/MS/MS Determination of Benzodiazepines in Human Urine: 1000 Samples per 12 Hours, Anal. Chem., Jul.1, 1999, pp. 2294-2300, vol. 71, No. 13.

* cited by examiner

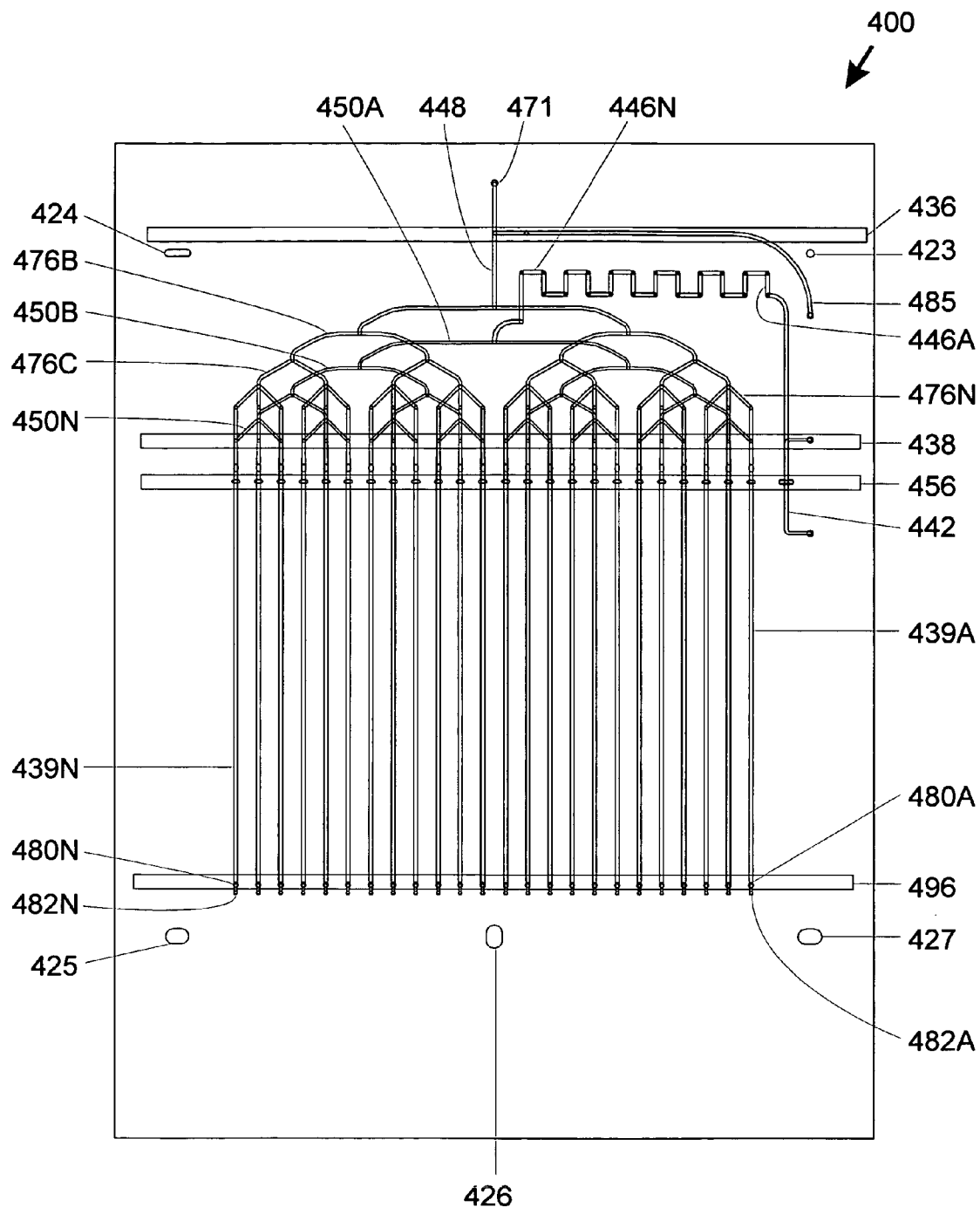
FIG._1

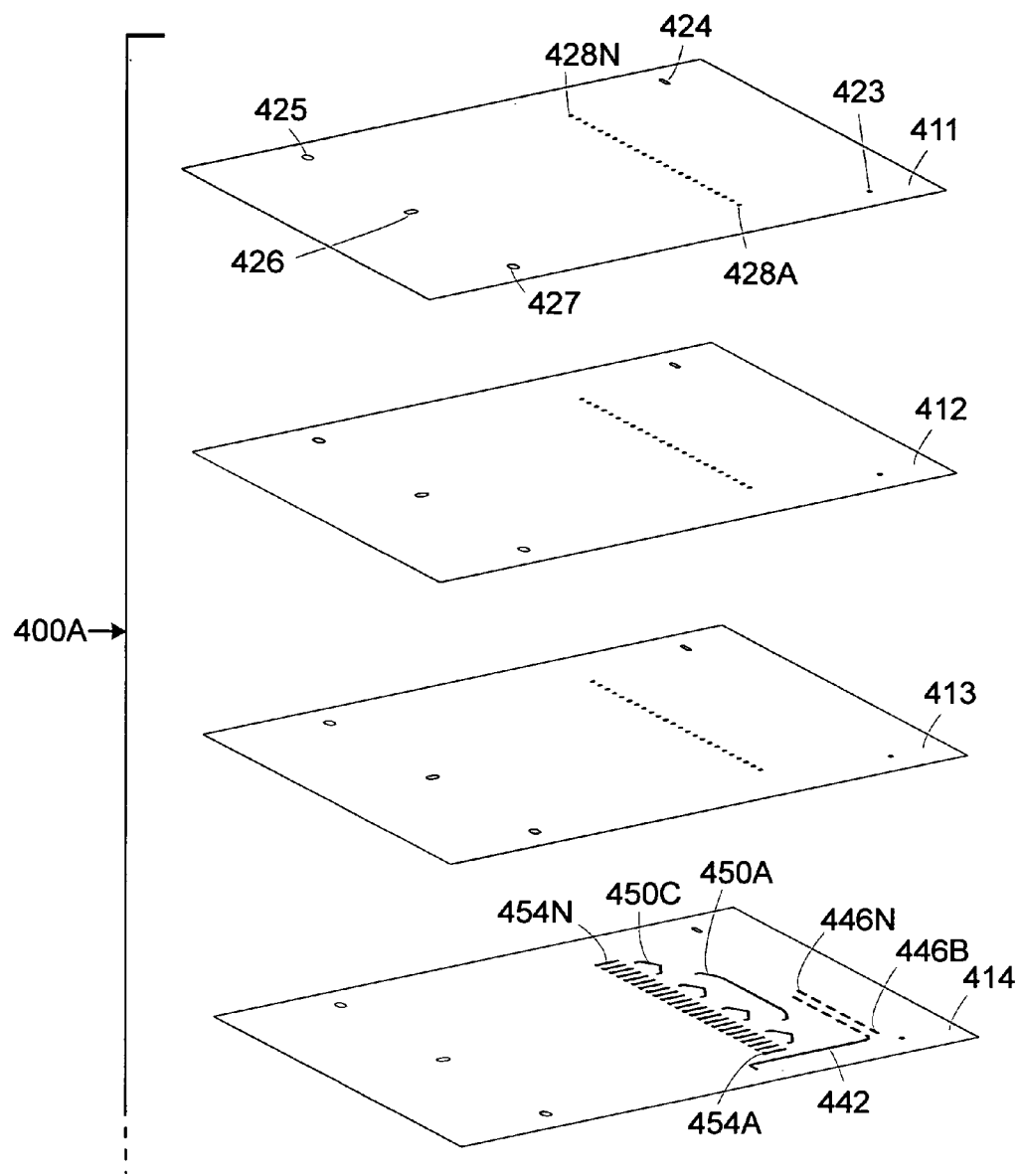
FIG._2A

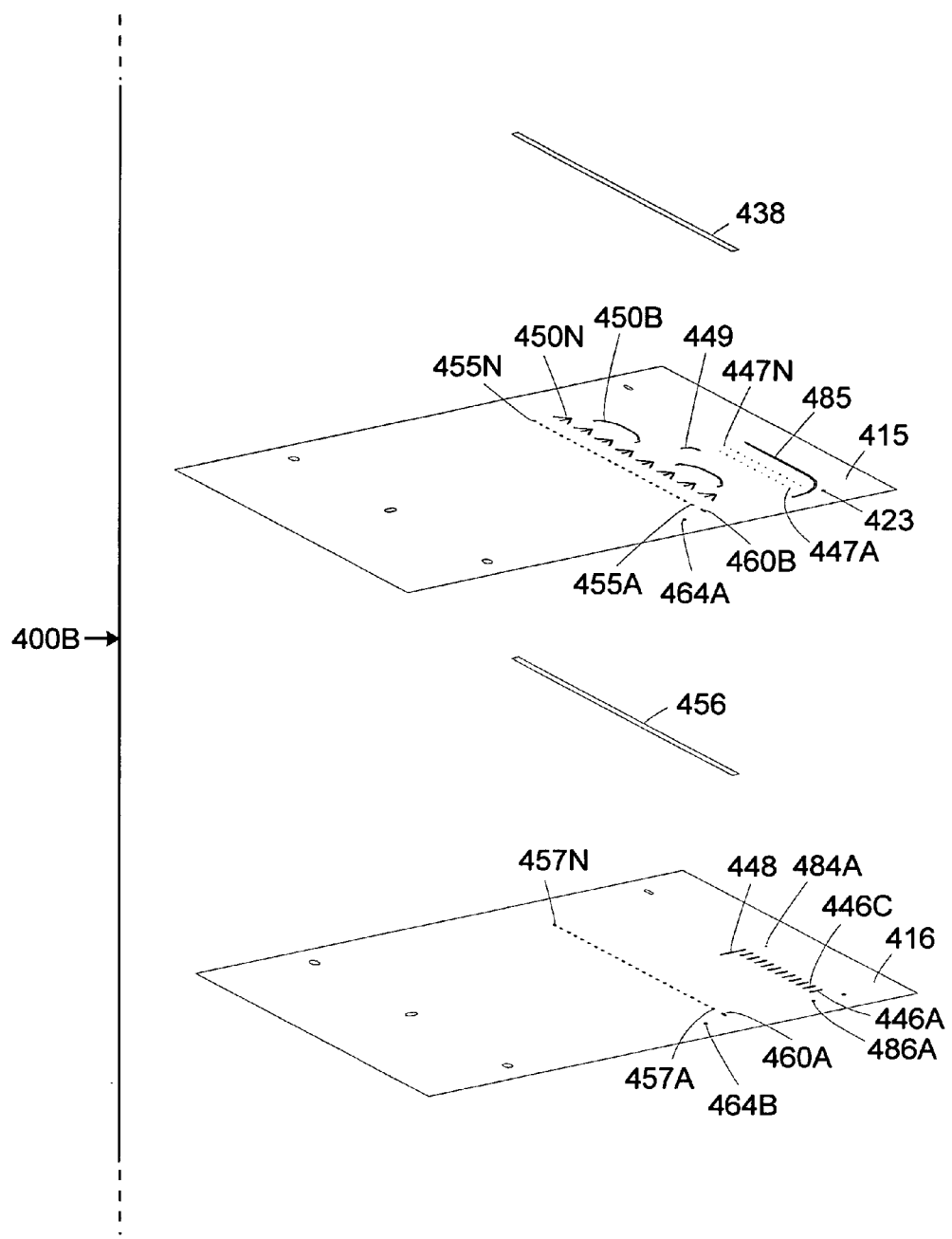
FIG._2B

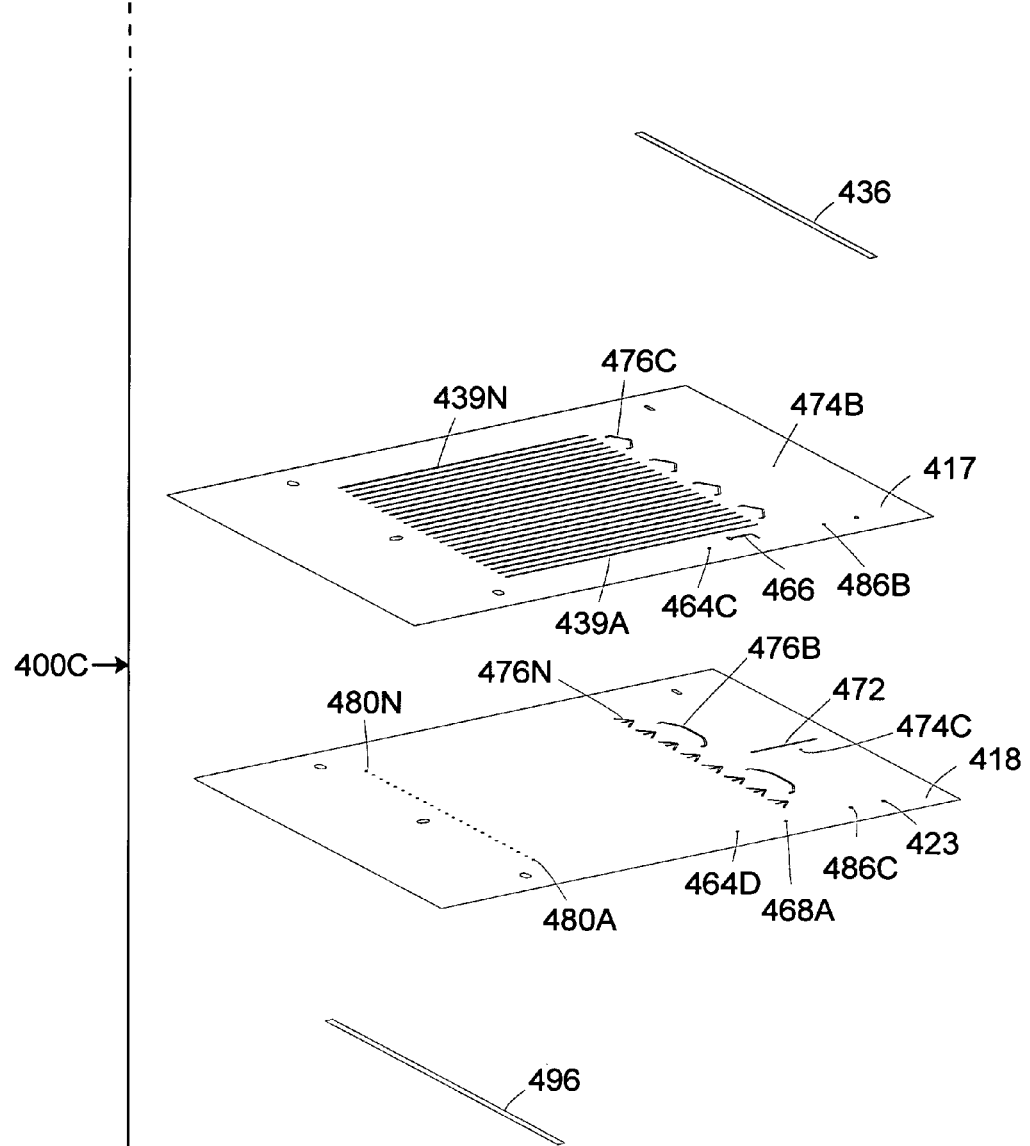
FIG._2C

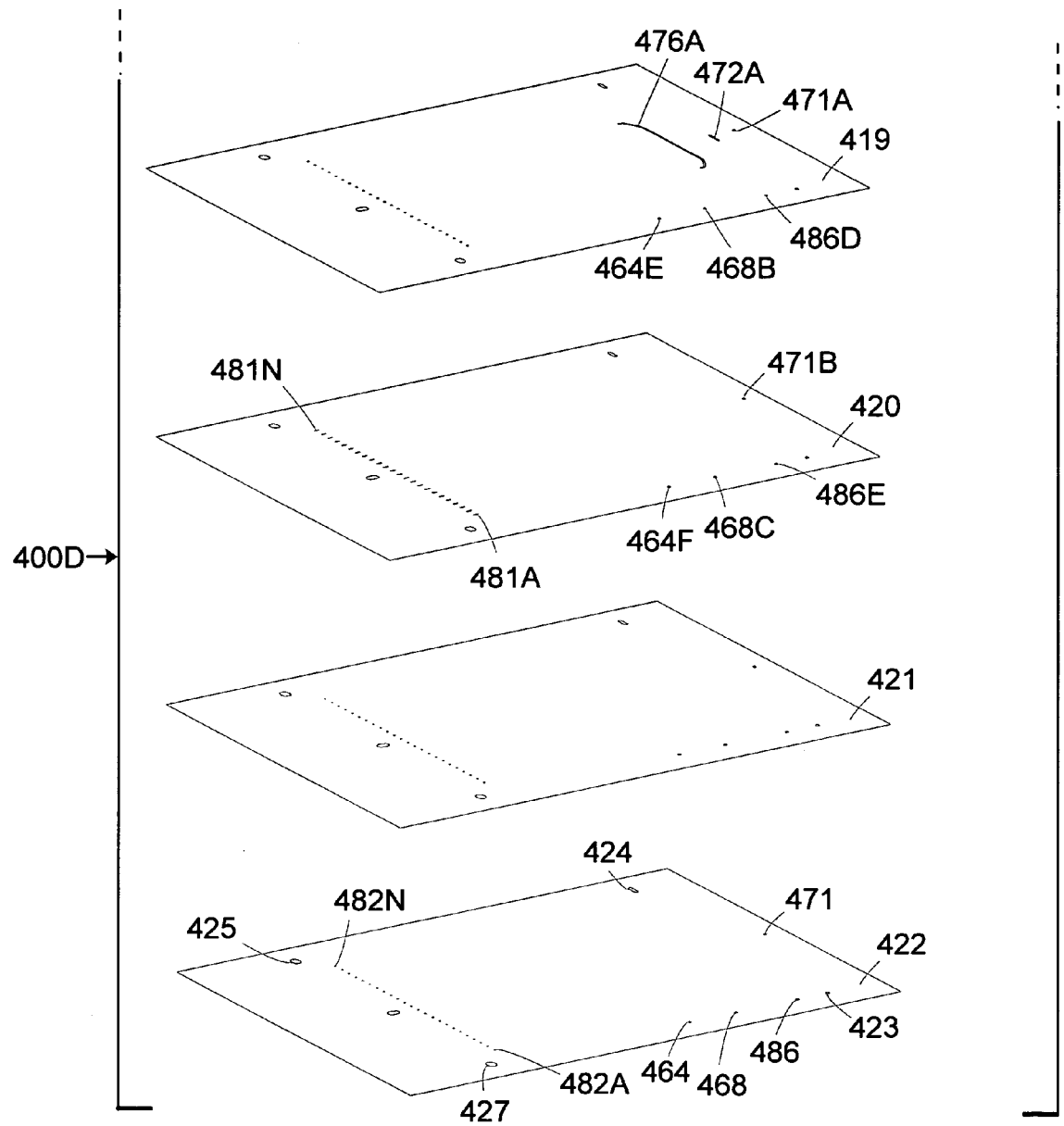
FIG._2D

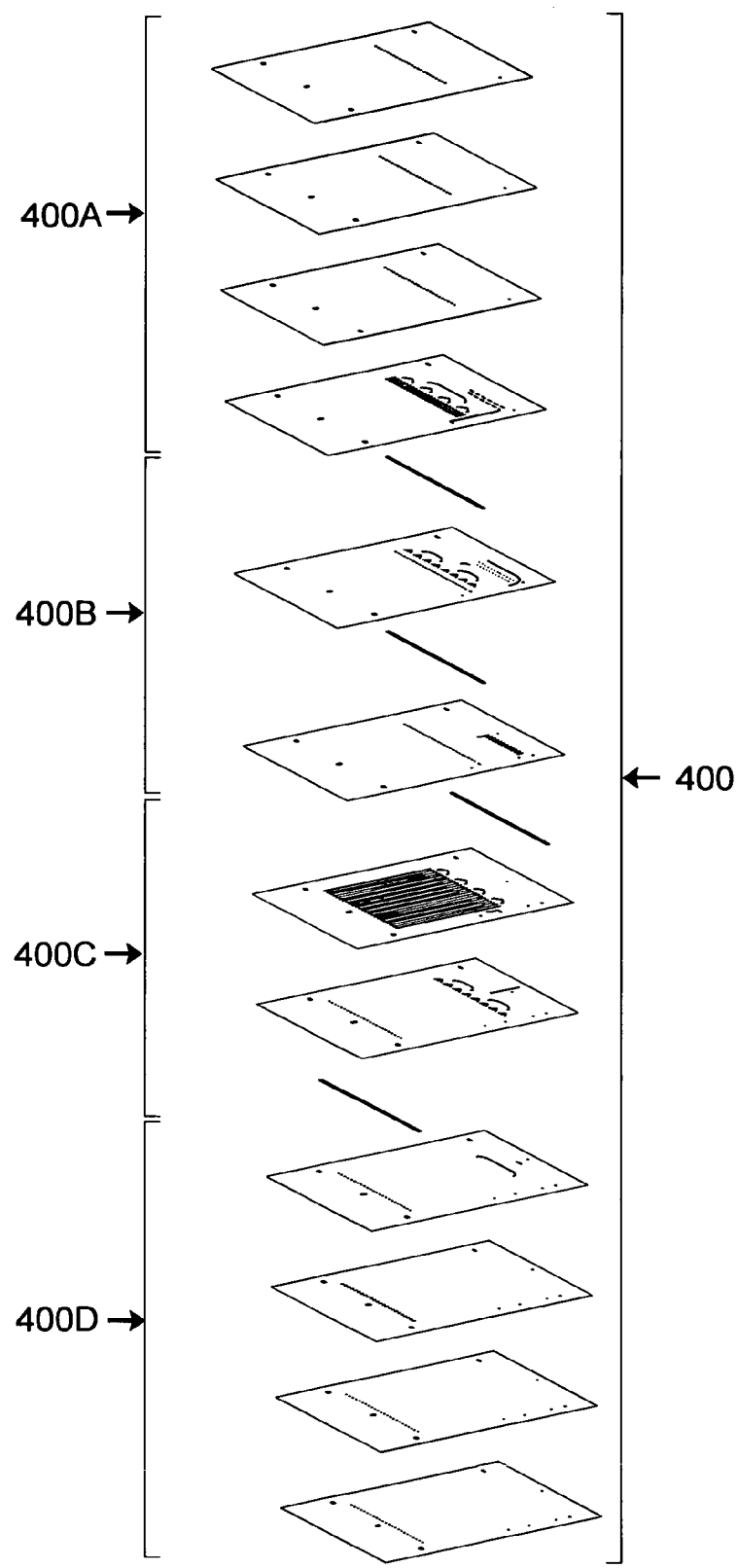
FIG._2E

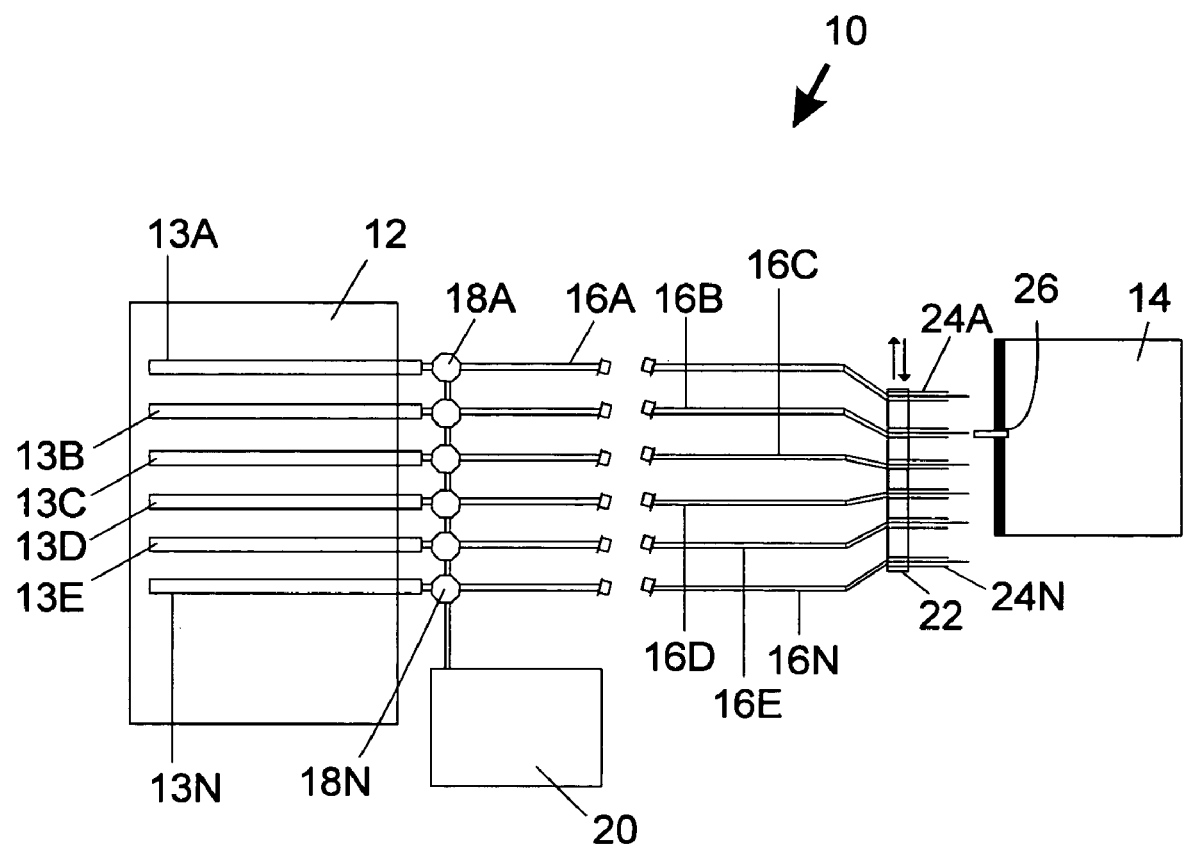
FIG. _3

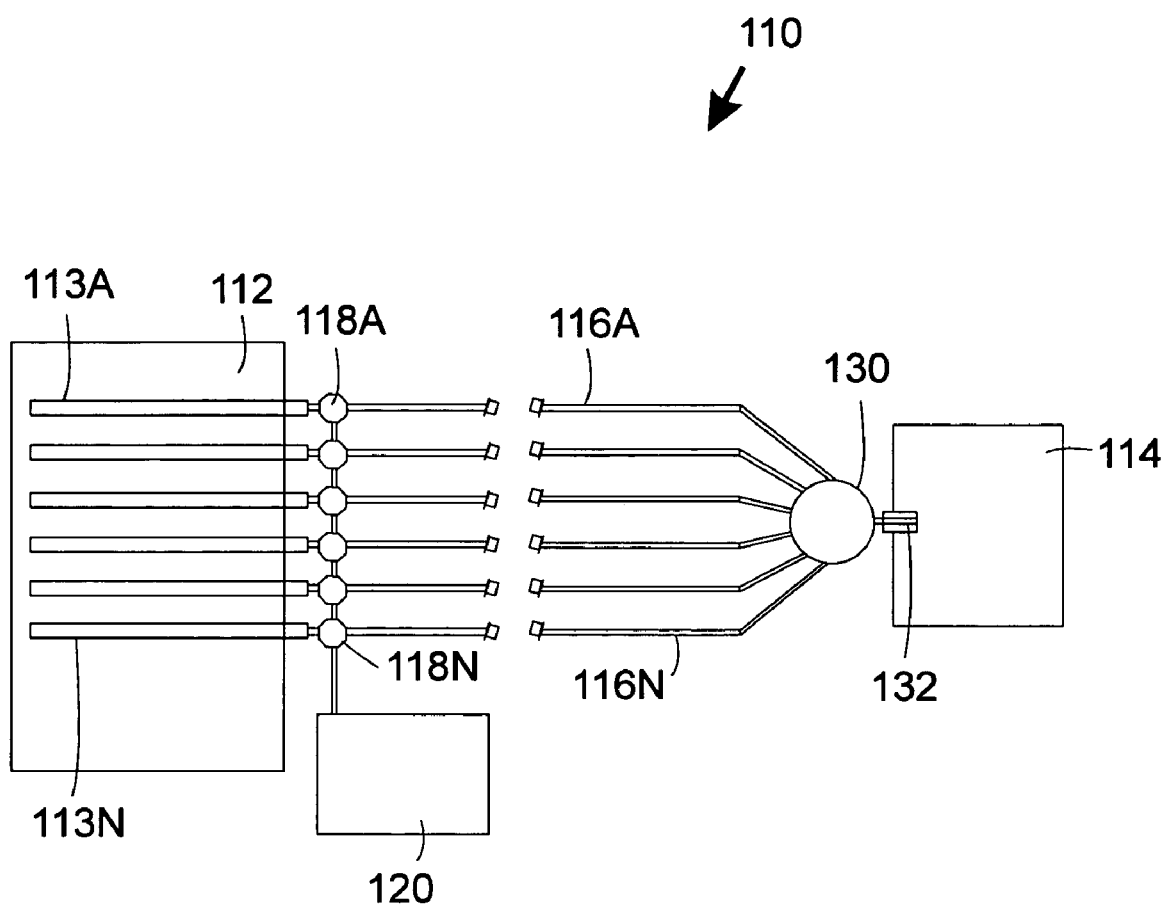
FIG. _4

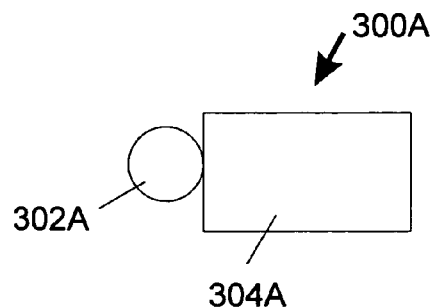
FIG. _6A
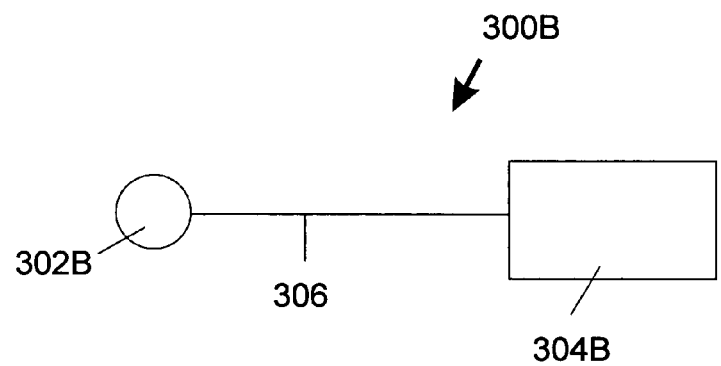
FIG. _6B
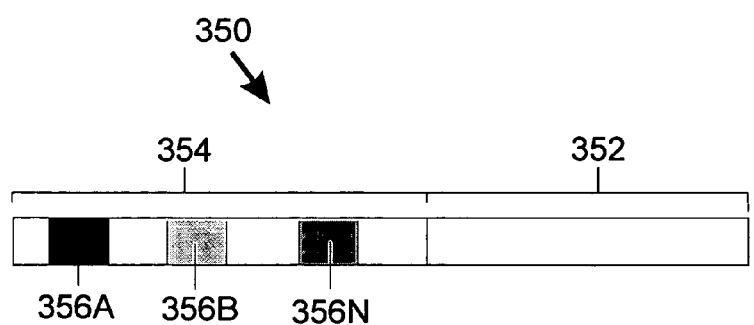
FIG. _7

SYSTEMS AND METHODS FOR HIGH THROUGHPUT SAMPLE ANALYSIS

STATEMENT OF RELATED APPLICATION(S)

This application claims benefit of the following commonly assigned U.S. patent applications Ser. No. 60/401,912 filed on Aug. 8, 2002, Ser. No. 10/637,234 filed on Aug. 8, 2003, now U.S. Pat. No. 6,812,458 Ser. No. 60/506,452 filed on Sep. 26, 2003, and Ser. No. 10/951,255 filed on Sep. 25, 2004, each of which is hereby incorporated by reference herein.

FIELD OF THE INVENTION

The present invention relates to high throughput systems for analyzing samples by both liquid phase separation methods and mass spectrometry.

BACKGROUND OF THE INVENTION

Recent developments in the pharmaceutical industry and in combinatorial chemistry have exponentially increased the number of potentially useful compounds, each of which must be characterized in order to identify their active components and/or establish processes for their synthesis. To more quickly analyze these compounds, researchers have sought to automate analytical processes and to implement analytical processes in parallel.

One useful analytical process is chromatography, which encompasses a number of methods that are used for separating ions or molecules that are dissolved in or otherwise mixed into a solvent. Liquid chromatography ("LC") is a physical method of separation wherein a liquid "mobile phase" (typically consisting of one or more solvents) carries a sample containing multiple constituents or species through a separation medium or "stationary phase." Various types of mobile phases and stationary phases may be used. Stationary phase material typically includes a liquid-permeable medium such as packed granules (particulate material) disposed within a tube (or other channel boundary). The packed material contained by the tube or similar boundary is commonly referred to as a "separation column." High pressure is often used to obtain a close-packed column with a minimal void between each particle, since better resolution during use is typically obtained from more tightly packed columns. As an alternative to packed particulate material, a porous monolith or similar matrix may be used. So-called "high performance liquid chromatography" ("HPLC") refers to efficient separation methods that are typically performed at high operating pressures.

Typical interactions between stationary phases and solutes include adsorption, ion-exchange, partitioning, and size exclusion. Examples of types of stationary phases to support such interactions are solids, ionic groups on a resin, liquids on an inert solid support, and porous or semi-porous inert particles, respectively. Commonly employed base materials include silica, alumina, zirconium, or polymeric materials. A stationary phase material may act as a sieve to perform simple size exclusion chromatography, or the stationary phase may include functional groups (e.g., chemical groups) to perform other (e.g., adsorption or ion exchange separation) techniques.

Mobile phase is forced through the stationary phase using means such as, for example, one or more pumps, gravity, voltage-driven electrokinetic flow, or other established means for generating a pressure differential. After sample is injected into the mobile phase, such as with a conventional loop valve, components of the sample will migrate according to interactions with the stationary phase and the flow of such components are retarded to varying degrees. Individual sample components may reside for some time in the stationary phase (where their velocity is essentially zero) until conditions (e.g., a change in solvent concentration) permit a component to emerge from the column with the mobile phase. In other words, as the sample travels through voids or pores in the stationary phase, the sample may be separated into its constituent species due to the attraction of the species to the stationary phase. The time a particular constituent spends in the stationary phase relative to the fraction of time it spends in the mobile phase will determine its velocity through the column. Following separation in an LC column, the output or eluate stream contains series of regions having an elevated concentration of individual component species. Thus, HPLC acts to provide relatively pure and discrete samples of each of the components of a compound. Gradient separations using conventional HPLC systems are typically performed within intervals of roughly five to ten minutes, followed by a flush or rinse cycle before another sample is separated in the same separation column.

Following chromatographic separation in the column, the resulting eluate stream (consisting of mobile phase and sample) contains a series of regions having elevated concentrations of individual species, which can be detected by various flow-through techniques including spectrophotometric (e.g., UV-Vis), fluorimetric, refractive index, electrochemical, or radioactivity detection. Liquid chromatography with flow-through detection generally provides signal response that is proportional to analyte amount or concentration. As a result, LC is well suited for quantitative analysis, but it is difficult to identify or characterize individual components using only LC, particularly when novel or previously uncharacterized compounds are used.

Another important analytical technique that can complement LC analysis is mass spectrometry ("MS"), which is widely used in many industrial and academic settings. MS permits molecular mass to be measured by determining the mass-to-charge ratio ("m/z") of ions generated from target molecules. A mass spectrometer typically includes a source for generating ions from a sample and delivering them into the gas phase, an analyzer for separating and sorting the ions, and a detector for sensing the ions as they are sorted. MS is a fast analytical technique that typically provides an output spectrum displaying ion intensity as a function of m/z. The benefit of using MS is that it can provide unique information about the chemical composition of the analyte—information that is much more specific than that can be obtained using flow-through detectors used with most conventional LC systems. Knowing the mass and composition of a desired molecule is especially important for pharmaceutical research, particularly in the synthesis of novel and uncharacterized molecules. The ability to qualitatively identify molecules using MS complements the quantitative capabilities of LC, thus providing a second dimension to the chromatographic analysis.

Various mass spectrometric techniques are known, including time-of-flight ("TOF"), quadrupole, and ion trap. In a TOF analyzer, ions are separated by differences in their velocities as they move in a straight path toward a collector in order of increasing mass-to-charge ratio. In a TOF MS, ions of a like charge are simultaneously emitted from the source with the same initial kinetic energy. Those with a lower mass will have a higher velocity and reach the detector earlier than ions with a higher mass. In a quadrupole device, a quadrupolar electrical field (comprising radio frequency and direct-current components) is used to separate ions. An ion trap (e.g., quadrupole-based) can trap and mass-analyze ions using a three-dimensional quadrupolar radio frequency electric field. In ion trap instruments, ions of increasing mass-to-charge ratio successively become unstable as the radio frequency voltage is scanned.

Various conventional ionization techniques may be used with mass spectrometry. One prevalent technique is electrospray ionization (ESI), which is a "soft" ionization technique. That is, ESI does not rely on extremely high temperatures or extremely high voltages to accomplish ionization, which is advantageous for the analysis of large, complex molecules that tend to decompose under harsh conditions. In an ESI interface, highly charged droplets of analyte dispersed from a capillary in an electric field are evaporated (typically assisted by the application of a drying gas), and the resulting desolvated charged ions are drawn into a MS inlet. Other known ionization techniques include: chemical ionization (which ionizes volatilized molecules by reaction with reagent gas ions); field ionization (which produces ions by subjecting a sample to a strong electric field gradient); spark-source desorption (which uses electrical discharges or sparks to desorb ions from samples); laser desorption (which uses a photon beam to desorb sample molecules); matrix-assisted laser desorption ionization or "MALDI" (which produces ions by laser desorbing sample molecules from a solid or liquid matrix containing a highly UV-absorbing substance); fast atom bombardment or "FAB" (which uses beams of neutral atoms to ionize compounds from the surface of a liquid matrix); and plasma desorption (which uses very high-energy ions to desorb and ionize molecules in solid-film samples).

By coupling the output of an HPLC system to a MS system, it becomes possible to both quantify and identify the components of a sample. There exist challenges, however, in providing efficient integrated HPLC/MS systems. Conventional MS systems are capable of much faster sample analysis than HPLC systems, and are much more expensive by a factor of roughly four to five times the cost of a single-column HPLC system. Integrated HPLC/MS systems including a single HPLC column coupled to a MS by way of an ESI interface are known, but they suffer from limited utility since the overall system throughput is limited by the HPLC column, which requires several minutes to separate a single sample. In other words, a HPLC/MS system having only a single HPLC column fails to efficiently utilize the rapid analytical capabilities of a mass spectrometer.

High throughput HPLC/MS systems having multiple HPLC columns coupled to a single MS are also known and provide greater separation efficiency compared to single-column HPLC/MS systems. Such systems, however, still suffer from limited utility. Examples are provided in U.S. Pat. No. 6,410,915 to Bateman et al.; U.S. Pat. No. 6,191,418 to Hindsgaul et al.; U.S. Pat. No. 6,066,848 to Kassel et al.; and U.S. Pat. No. 5,872,010 to Karger et al., each showing some variation of a multiplexed HPLC/MS system where the outputs of multiple simultaneously-operated separation columns are periodically sampled by a single MS device. However, in such real-time multiplexed HPLC/MS systems, the MS can sample an eluate stream from only one LC column at a given time. While one stream is being analyzed, the others must continue to flow, as these systems have no storage capacity. The streams that are not being directed to the MS at any point in time are directed to waste, inherently resulting in data loss. To mitigate this data loss, MS sampling must occur very quickly. The MS instrument thus receives very small plugs of sample, reducing the ability of the instrument to integrate data in order to eliminate noise and resulting in reduced signal clarity.

Another staggered 'parallel' approach is described in U.S. Pat. No. 6,318,157 to Corso et al ("Corso"). Corso describes a multiplexed HPLC/MS device where gradient separations are performed by staggering the initiation of separations in four separate columns by using input lines of varying length. In this manner, each output stream may be analyzed continuously by the MS instrument. The staggering technique taught by Corso effectively acts as four serial separations. While some efficiencies are gained by not having to prepare a single column four times, the overall run time of the four columns run in a stagger is much longer than the run time of four columns run simultaneously. Additionally, the necessary amount of stagger (i.e., the length of each input line) must be calculated in advance to insure that regions of interest have no temporal overlap, which may be difficult when characterizing unknown compounds. Corso also suggests that the staggering of inputs is not necessary for isocratic separations; however, Corso does not indicate how overlap of regions of interest can be avoided. Presumably, a sampling technique is used, thus creating the same data loss and signal clarity issues discussed above.

Accordingly, there exists a need for improved HPLC/MS systems that permit parallel analysis of multiple samples. Advantageous system characteristics would include scalability to permit a large number of samples to be analyzed simultaneously at a low cost per analysis with minimal loss of data and/or signal clarity. Ideally, an improved system would operate rapidly and be comparatively simple and inexpensive to build and operate.

BRIEF DESCRIPTION OF THE DRAWINGS

FIG. 1 is a top view of a multi-layer microfluidic device containing twenty-four separation columns suitable for performing pressure-driven liquid chromatography.

FIG. 2A is an exploded perspective view of a first portion, including the first through fourth layers, of the microfluidic device shown in FIG. 1.

FIG. 2B is an exploded perspective view of a second portion, including the fifth and sixth layers, of the microfluidic device shown in FIG. 1.

FIG. 2C is an exploded perspective view of a third portion, including the seventh and eighth layers, of the microfluidic device shown in FIG. 1.

FIG. 2D is an exploded perspective view of a fourth portion, including the ninth through twelfth layers, of the microfluidic device shown in FIG. 1.

FIG. 2E is a reduced size composite of FIGS. 2A–2D showing an exploded perspective view of the microfluidic device of FIG. 1.

FIG. 3 is a top diagrammatic view of one embodiment of a fluid handling system for multiplexed HPLC/MS analysis according to the present invention.

FIG. 4 is a top diagrammatic view of another embodiment of a fluid handling system for multiplexed HPLC/MS analysis according to the present invention.

FIG. 6A is a schematic of an experimental system used to measure performance characteristics of a fluid injector. FIG. 6B is a schematic of an experimental system used to measure performance characteristics of a fluid injector used in combination with a storage line.

FIG. 7 is a block diagram illustrating the components of an output stream produced by a separation column.

Figure 5:
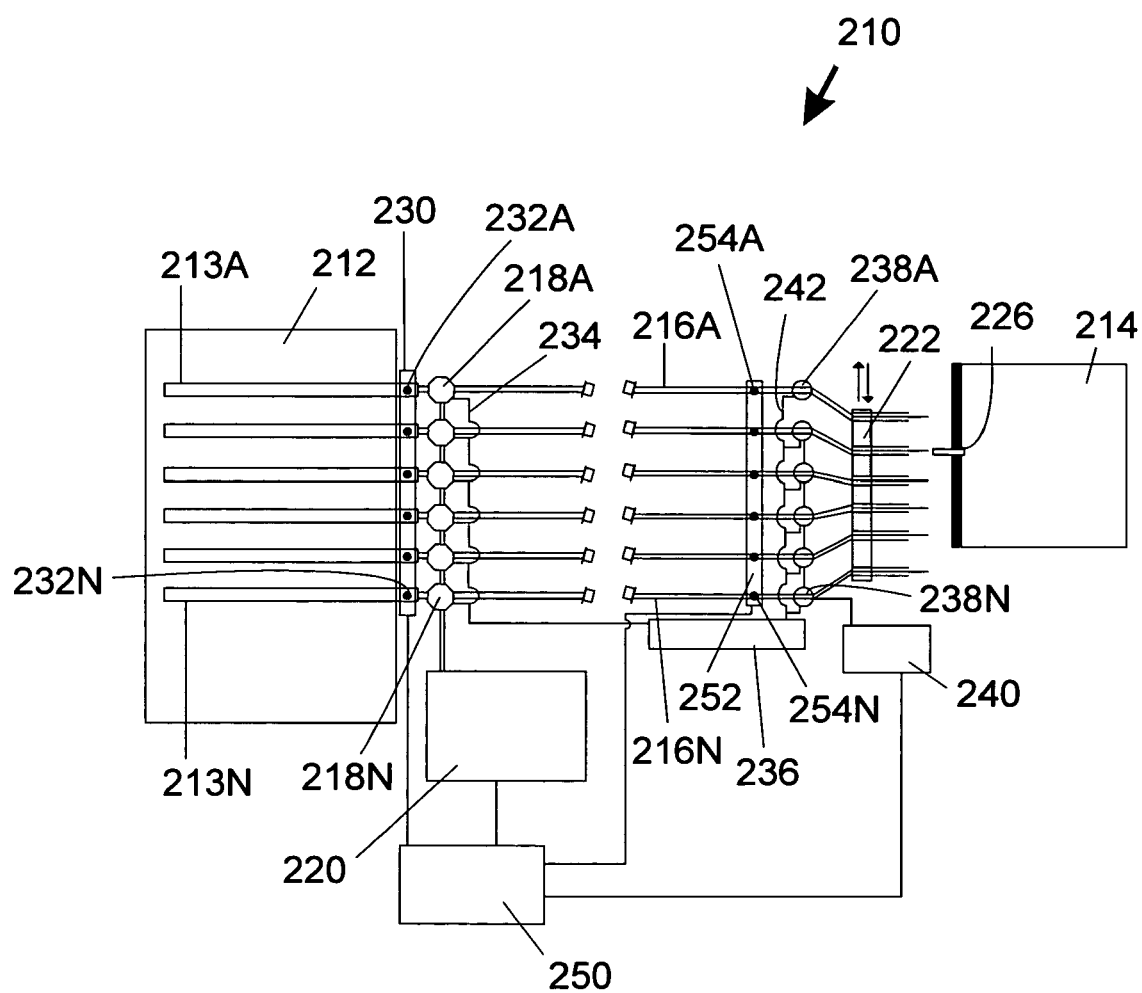
FIG. 5 is a top diagrammatic view of another embodiment of a fluid handling system for multiplexed HPLC/MS analysis according to the present invention.

None of the figures are drawn to scale unless indicated otherwise. The size of one figure relative to another is not intended to be limiting, since certain figures and/or features may be expanded to promote clarity in the description.

DETAILED DESCRIPTION OF PREFERRED EMBODIMENTS OF THE INVENTION

Definitions

The terms "column" or "separation column" as used herein are used interchangeably and refer to a region of a fluidic device that contains stationary phase material and is adapted to perform a separation process.

The term "fluidic distribution network" refers to an interconnected, branched group of channels and/or conduits capable of adapted to divide a fluid stream into multiple substreams.

The term "frit" refers to a liquid-permeable material adapted to retain stationary phase material within a separation column.

The term "liquid phase separation region" as used herein refers to any region adapted to perform a liquid phase chemical or biochemical analytical process such as chromatographic, electrophoretic, electrochromatographic, immunoaffinity, gel filtration, and/or density gradient separation. A separation column is one type of a liquid phase separation region.

The term "mass spectrometer" as used herein refers to an analytical component that serves to separate ions electromagnetically based on their charge/mass ratio and detect them.

The term "microfluidic" as used herein refers to structures or devices through which one or more fluids are capable of being passed or directed and having at least one dimension less than about 500 microns.

The term "packed" as used herein refers to the state of being substantially filled with a packing material (such as a particulate material).

The term "parallel" as used herein refers to the ability to concomitantly or substantially concurrently process two or more separate fluid volumes, and does not necessarily refer to a specific channel or chamber structure or layout.

The term "plurality" as used herein refers to a quantity of two or more.

The term "stencil" as used herein refers to a material layer or sheet that is preferably substantially planar through which one or more variously shaped and oriented portions have been cut or otherwise removed through the entire thickness of the layer, and that permits substantial fluid movement within the layer (e.g., in the form of channels or chambers, as opposed to simple through-holes for transmitting fluid through one layer to another layer). The outlines of the cut or otherwise removed portions form the lateral boundaries of microstructures that are formed when a stencil is sandwiched between other layers such as substrates and/or other stencils.

The term "storage region," "storage element," and "storage line" as may be used herein are used substantially interchangeably and refer to any structure adapted to convey and store a fluid while maintaining the integrity of an output stream of a liquid phase separation region, including, but not limited to tubes, conduits, channels, and chambers. A column, including, but not limited to tubes, conduits, and channels.

Microfluidic Devices Generally

In one embodiment, one or more liquid phase separation regions may be provided in a microfluidic device. Traditionally, microfluidic devices have been fabricated from rigid materials such as silicon or glass substrates using surface micromachining techniques to define open channels and then affixing a cover to a channel-defining substrate to enclose the channels. There now exist a number of well-established techniques for fabricating microfluidic devices, including machining, micromachining (including, for example, photolithographic wet or dry etching), micromolding, LIGA, soft lithography, embossing, stamping, surface deposition, and/or combinations thereof to define apertures, channels or chambers in one or more surfaces of a material or that penetrate through a material.

A preferred method for constructing microfluidic devices utilizes stencil fabrication, which includes the lamination of at least three device layers including at least one stencil layer or sheet defining one or more microfluidic channels and/or other microstructures. As noted previously, a stencil layer is preferably substantially planar and has a channel or chamber cut through the entire thickness of the layer to permit substantial fluid movement within that layer. Various means may be used to define such channels or chambers in stencil layers. For example, a computer-controlled plotter modified to accept a cutting blade may be used to cut various patterns through a material layer. Such a blade may be used either to cut sections to be detached and removed from the stencil layer, or to fashion slits that separate regions in the stencil layer without removing any material. Alternatively, a computer-controlled laser cutter may be used to cut portions through a material layer. While laser cutting may be used to yield precisely dimensioned microstructures, the use of a laser to cut a stencil layer inherently involves the removal of some material. Further examples of methods that may be employed to form stencil layers include conventional stamping or die-cutting technologies, including rotary cutters and other high throughput auto-aligning equipment (sometimes referred to as converters). The above-mentioned methods for cutting through a stencil layer or sheet permits robust devices to be fabricated quickly and inexpensively compared to conventional surface micromachining or material deposition techniques that are conventionally employed to produce microfluidic devices.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. When assembled in a microfluidic device, the top and bottom surfaces of stencil layers mate with one or more adjacent layers (such as stencil layers or substrate layers) to form a substantially enclosed device, typically having at least one inlet port and at least one outlet port.

A wide variety of materials may be used to fabricate microfluidic devices having sandwiched stencil layers, including polymeric, metallic, and/or composite materials, to name a few. Various preferred embodiments utilize porous materials including filtration media. Substrates and stencils may be substantially rigid or flexible. Selection of particular materials for a desired application depends on numerous factors including: the types, concentrations, and residence times of substances (e.g., solvents, reactants, and products) present in regions of a device; temperature; pressure; pH; presence or absence of gases; and optical properties. For instance, particularly desirable polymers include polyolefins, more specifically polypropylenes, and vinyl-based polymers.

Various means may be used to seal or bond layers of a device together. For example, adhesives may be used. In one embodiment, one or more layers of a device may be fabricated from single- or double-sided adhesive tape, although other methods of adhering stencil layers may be used. Portions of the tape (of the desired shape and dimensions) can be cut and removed to form channels, chambers, and/or apertures. A tape stencil can then be placed on a supporting substrate with an appropriate cover layer, between layers of tape, or between layers of other materials. In one embodiment, stencil layers can be stacked on each other. In this embodiment, the thickness or height of the channels within a particular stencil layer can be varied by varying the thickness of the stencil layer (e.g., the tape carrier and the adhesive material thereon) or by using multiple substantially identical stencil layers stacked on top of one another. Various types of tape may be used with such an embodiment. Suitable tape carrier materials include but are not limited to polyesters, polycarbonates, polytetrafluoroethlyenes, polypropylenes, and polyimides. Such tapes may have various methods of curing, including curing by pressure, temperature, or chemical or optical interaction. The thickness of these carrier materials and adhesives may be varied.

Device layers may be directly bonded without using adhesives to provide high bond strength (which is especially desirable for high-pressure applications) and eliminate potential compatibility problems between such adhesives and solvents and/or samples. For example, in one embodiment, multiple layers of 7.5-mil (188 micron) thickness "Clear Tear Seal" polypropylene (American Profol, Cedar Rapids, Iowa) including at least one stencil layer may be stacked together, placed between glass platens and compressed to apply a pressure of 0.26 psi (1.79 kPa) to the layered stack, and then heated in an industrial oven for a period of approximately five hours at a temperature of 154° C. to yield a permanently bonded microstructure well-suited for use with high-pressure column packing methods. In another embodiment, multiple layers of 7.5-mil (188 micron) thickness "Clear Tear Seal" polypropylene (American Profol, Cedar Rapids, Iowa) including at least one stencil layer may be stacked together. Several microfluidic device assemblies may be stacked together, with a thin foil disposed between each device. The stack may then be placed between insulating platens, heated at 152° C. for about 5 hours, cooled with a forced flow of ambient air for at least about 30 minutes, heated again at 146° C. for about 15 hours, and then cooled in a manner identical to the first cooling step. During each heating step, a pressure of about 0.37 psi (2.55 kPa) is applied to the microfluidic devices.

Notably, stencil-based fabrication methods enable very rapid fabrication of devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

In addition to the use of adhesives and the adhesiveless bonding method discussed above, other techniques may be used to attach one or more of the various layers of microfluidic devices useful with the present invention, as would be recognized by one of ordinary skill in attaching materials. For example, attachment techniques including thermal, chemical, or light-activated bonding steps; mechanical attachment (such as using clamps or screws to apply pressure to the layers); and/or other equivalent coupling methods may be used.

Liquid Phase Separation (e.g. Chromatography) Devices

One advantage of performing a liquid phase separation process such as chromatography in a microfluidic format is that multiple separations can be performed in parallel with a single liquid phase separation system. Although the following examples are directed primarily to liquid chromatography system and devices, one skilled in the art will recognize that various different types of liquid phase separation processes, such as chromatographic, electrophoretic, electrochromatographic, immunoaffinity, gel filtration, and/or density gradient separations, may be utilized in systems and methods according to the present invention utilizing the teachings provided herein.

If multiple chromatography columns are provided in a single separation device, then such a device preferably has at least one associated fluidic distribution network to permit operation with a minimum number of expensive (typically external) system components such as pumps and pulse dampers. One example of a multi-column microfluidic separation device suitable for performing pressure-driven liquid chromatography is provided in FIG. 1 and FIGS. 2A–2E. The device 400 includes twenty-four parallel separation channels 439A–439N containing stationary phase material. (Although FIG. 1 and FIGS. 2A–2E show the device 400 having eight separation columns 439A–439N, it will be readily apparent to one skilled in the art that any number of columns 439A–439N may be provided. For this reason, the designation "N" represents a variable and could represent any desired number of columns. This convention is used throughout this document.)

The device 400 may be constructed with twelve device layers 411–422, including multiple stencil layers 414–420 and two outer or cover layers 411, 422. Each of the twelve device layers 411–422 defines five alignment holes 423–427 (with hole 424 configured as a slot), which may be used in conjunction with external pins (not shown) to aid in aligning the layers during construction or in aligning the device 400 with an external interface (not shown) during a packing process or during operation of the device 400. Preferably, the device 400 is constructed with materials selected for their compatibility with chemicals typically utilized in performing high performance liquid chromatography, including, water, methanol, ethanol, isopropanol, acetonitrile, ethyl acetate, dimethyl sulfoxide, and mixtures thereof. Specifically, the device materials should be substantially non-absorptive of, and substantially non-degrading when placed into contact with, such chemicals. Suitable device materials include polyolefins such as polypropylene, polyethylene, and copolymers thereof, which have the further benefit of being substantially optically transmissive so as to aid in performing quality control routines (including checking for fabrication defects) and in ascertaining operational information about the device or its contents. For example, each device layer 411–422 may be fabricated from 7.5 mil (188 micron) thickness "Clear Tear Seal" polypropylene (American Profol, Cedar Rapids, Iowa).

Broadly, the device 400 includes various structures adapted to distribute particulate-based slurry material among multiple separation channels 439A–439N (to become separation columns upon addition of stationary phase material), to retain the stationary phase material within the device 400, to mix and distribute mobile phase solvents among the separation channels 439A–439N, to receive samples, to convey eluate streams from the device 400, and to convey a waste stream from the device 400.

The first through third layers 411–413 of the device 400 are identical and define multiple sample ports/vias 428A–428N that permit samples to be supplied to channels 454A–454N defined in the fourth layer 414. While three separate identical layers 411–413 are shown (to promote strength and increase the aggregate volume of the sample ports/vias 428A–428N to aid in sample loading), a single equivalent layer (not shown) having the same aggregate thickness could be substituted. The fourth through sixth layers 414–416 define a mobile phase distribution network 450 (including elements 450A–450N) adapted to split a supply of mobile phase solvent among twenty-four channel loading segments 454A–454N disposed just upstream of a like number of separation channels (columns) 439A–439N. Upstream of the mobile phase distribution network 450, the fourth through seventh layers 414–417 further define mobile phase channels 448–449 and structures for mixing mobile phase solvents, including a long mixing channel 442, wide slits 460A–460B, alternating channel segments 446A–446N (defined in the fourth and sixth layers 414–416) and vias 447A–447N (defined in the fifth layer 415).

Preferably, the separation channels 439A–439N are adapted to contain stationary phase material such as, for example, silica-based particulate material to which hydrophobic C-18 (or other carbon-based) functional groups have been added. One difficulty associated with prior microfluidic devices has been retaining small particulate matter within separation columns during operation. The present device 400 overcomes this difficulty by the inclusion of a downstream porous frit 496 and a sample loading porous frit 456. Each of the frits 456, 496 (and frits 436, 438) may be fabricated from strips of porous material, e.g., 1-mil thickness Celgard 2500 membrane (55% porosity, 0.209×0.054 micron pore size, Celgard Inc., Charlotte, N.C.) and inserted into the appropriate regions of the stacked device layers 411–422 before the layers 411–422 are laminated together. The average pore size of the frit material should be smaller than the average size of the stationary phase particles. Preferably, an adhesiveless bonding method such as one of the methods described previously herein is used to bond the device layers 411–422 (and frits 436, 438, 456, 496) together. Such methods are desirably used to promote high bond strength (e.g., to withstand operation at high internal pressures of preferably at least about 100 psi (690 kPa), more preferably at least about 500 psi (3450 kPa)) and to prevent undesirable interaction between any bonding agent and solvents and/or samples to be supplied to the device 400.

A convenient method for packing stationary phase material within the separation channels 439A–439N is to provide it to the device in the form of a slurry (i.e., particulate material mixed with a solvent such as acetonitrile). Slurry is supplied to the device 400 by way of a slurry inlet port 471 and channel structures defined in the seventh through ninth device layers 417–419. Specifically, the ninth layer 419 defines a slurry via 471A, a waste channel segment 472A, and a large forked channel 476A. The eighth device layer 418 defines two medium forked channels 476B and a slurry channel 472 in fluid communication with the large forked channel 476A defined in the ninth layer 419. The eighth layer 418 further defines eight smaller forked channels 476N each having three outlets, and twenty-four column outlet vias 480A–480N. The seventh layer 417 defines four small forked channels 476C in addition to the separation channels 439A–439N. In the aggregate, the large, medium, small, and smaller forked channels 476A–476N form a slurry distribution network that communicates slurry from a single inlet (e.g., slurry inlet port 471) to twenty-four separation channels 439A–439N (to become separation columns 439A–439N upon addition of stationary phase material). Upon addition of particulate-containing slurry to the separation channels 439A–439N, the particulate stationary phase material is retained within the separation channels by one downstream porous frit 496 and by one sample loading porous frit 456. After stationary phase material is packed into the columns 439A–439N, a sealant (preferably substantially inert such as UV-curable epoxy) is added to the slurry inlet port 471 to prevent the columns from unpacking during operation of the device 400. The addition of sealant should be controlled to prevent blockage of the waste channel segment 472A.

To prepare the device 400 for operation, one or more mobile phase solvents may be supplied to the device 400 through mobile phase inlet ports 464, 468 defined in the twelfth layer 422. These solvents may be optionally premixed upstream of the device 400 using a conventional micromixer. Alternatively, these solvents are conveyed through several vias (464A–464F, 468A–468C) before mixing. One solvent is provided to the end of the long mixing channel 442, while the other solvent is provided to a short mixing segment 466 that overlaps the mixing channel 442 through wide slits 460A–460B defined in the fifth and sixth layers 415, 416, respectively. One solvent is layered atop the other across the entire width of the long mixing channel 442 to promote diffusive mixing. To ensure that the solvent mixing is complete, however, the combined solvents also flow through an additional mixer composed of alternating channel segments 446A–446N and vias 447A–447N. The net effect of these alternating segments 446A–446N and vias 447A–447N is to cause the combined solvent stream to contract and expand repeatedly, augmenting mixing between the two solvents. The mixed solvents are supplied through channel segments 448, 449 to the distribution network 450 including one large forked channel 450A each having two outlets, two medium forked channels 450B each having two outlets, four small forked channels 450C each having two outlets, and eight smaller forked channels 450N each having three outlets.

Each of the eight smaller forked channels 450A–450N is in fluid communication with three of twenty-four sample loading channels 454A–454N. Additionally, each sample loading channel 454A–454N is in fluid communication with a different sample loading port 428A–428N. Two porous frits 438, 456 are disposed at either end of the sample loading channels 454A–454N. While the first frit 438 technically does not retain any packing material within the device, it may be fabricated from the same material as the second frit 456, which does retain packing material within the columns 439A–439N by way of several vias 457A–457N. To prepare the device 400 for sample loading, solvent flow is temporarily interrupted, an external interface (not shown) previously covering the sample loading ports 428A–428N is opened, and samples are supplied through the sample ports 428A–428N into the sample loading channels 454A–454N. The first and second frits 438, 456 provide a substantial fluidic impedance that prevents fluid flow through the frits 438, 456 at low pressures. This ensures that the samples remain isolated within the sample loading channels 454A–454N during the sample loading procedure. Following sample loading, the sample loading ports 428A–428N are again sealed (e.g., with an external interface) and solvent flow is re-initiated to carry the samples onto the separation columns 439A–439N defined in the seventh layer 417.

While the bulk of the sample and solvent that is supplied to each column 439A–439N travels downstream through the columns 439A–439N, a small split portion of each travels upstream through the columns in the direction of the waste port 485. The split portions of sample and solvent from each column that travel upstream are consolidated into a single waste stream that flows through the slurry distribution network 476, through a portion of the slurry channel 472, then through the short waste segment 472A, vias 474C, 474B, a frit 436, a via 484A, a waste channel 485, vias 486A–486E, and through the waste port 486 to exit the device 400. The purpose of providing both an upstream and downstream path for each sample is to prevent undesirable cross-contamination from one separation run to the next, since this arrangement prevents a portion of a sample from residing in the sample loading channel during a first run and then commingling with another sample during a subsequent run.

Either isocratic separation (in which the mobile phase composition remains constant) or, more preferably, gradient separation (in which the mobile phase composition changes with time) may be performed. Following separation, the eluate may be analyzed by one or more detection techniques and/or collected for further analysis. Preferably, the eluate is analyzed using both flow-through optical-type detection (e.g., UV-Vis and/or fluorescence detection) and, subsequently, mass analysis such as mass spectrometry.

Other Multi-Column Separation Devices

Although multi-column microfluidic devices such as the device 400 are preferably used in an integrated multi-column separation and analysis (e.g., HPLC/MS) system, other formats, whether or not microfluidic, embodying multiple liquid phase separation process regions (e.g., columns) may be used. A multi-column HPLC apparatus may be any suitable device that includes multiple parallel separation columns. Multiple discrete tubular-type columns, multiple independent columns positioned within a single device, or any other suitable multi-column configuration may be used. Preferably, such columns are batch processed to impart similar performance characteristics, and such columns are preferably and connected by a common body structure. It will be readily understood by one skilled in the art that any form or configuration of HPLC columns may be used, the appropriate column, fabrication method and stationary phase material being selected to match the performance characteristics required for the particular separation(s). Representative parallel HPLC column devices and fabrication methods are provided in commonly assigned U.S. patent application Ser. No. 10/638,258 entitled "Multi-Column Separation Devices and Methods" filed Aug. 7, 2003, the disclosure of which is hereby incorporated by reference as if fully set forth herein.

Minimizing Post-Separation Band Broadening Generally

Systems and methods according to the present invention utilize storage means interposed between multiple liquid phase separation regions and a common mass spectrometer. In one embodiment, predetermined lengths of microfluidic tubing or conduits act as storage buffers for the output of each separation region. Because the storage buffers are microfluidic, there is minimal diffusion between sample bands and solvent and signal clarity is preserved. If desired, the entire output of each separation region may be stored before being discharged to a mass spectrometer.

One general concern associated with interfacing multiple HPLC columns (or other separation regions) to a single MS is that eluate components separated from the chromatography process will "smear" or mix before the mass of such components can be analyzed by the MS. Several HPLC/MS interface systems and techniques disclosed herein include eluate storage capability disposed between a group of HPLC columns and the inlet of an associated MS. In certain embodiments, each eluate storage element includes sufficient volume to contain substantially all of the eluate flowing from a single column (i.e., to store an entire chromatogram). In such embodiments, the eluate storage elements are preferably microfluidic to minimize diffusion of separated bands of analyte and thereby preserve signal clarity. Commercially available capillary tubing of microfluidic internal dimensions may advantageously be used. If desired, the non-species-containing portions of the eluate (i.e., at the beginning and end of a chromatographic separation run) may be directed to waste through valves before the portion (s) of interest are stored in the eluate storage elements.

Another strategy for reducing broadening or mixing between bands of separated eluate in storage lines includes providing a spacing medium between discrete bands. The spacing medium is preferably a fluid, more preferably a relatively inert gas such as nitrogen.

Preferred Analytical Systems and Methods

Referring to FIG. 3, a HPLC/MS analytical system 10 according to the present invention includes a microfluidic parallel HPLC apparatus 12 having six separation columns 13A–13N (i.e., six "channels"), a microfluidic storage line 16A–16N connected to each column 13A–13N and leading to a mass spectrometer 14. (Although FIG. 3 shows the system 10 having six channels 13A–13N and six microfluidic storage lines 16A–16N, it will be readily apparent to one skilled in the art that any number of channels 13A–13N and microfluidic storage lines 16A–16N may be provided. For this reason, the designation "N" is used to represent the last channel 13N and microfluidic storage line 16N, with the understanding that "N" represents a variable and could represent any desired number of microfluidic storage lines. This convention is used throughout this document.)

The HPLC apparatus 12 may be any suitable device that includes multiple separation columns 13A–13N adapted to operate in parallel. The columns 13A–13N may be integrated within a single microfluidic device or chip 12; multiple independent columns (not shown); multiple independent columns positioned within a single device (not shown); or any other suitable configuration. The HPLC system 12 and its component columns 13A–13N may be manufactured by any suitable method, such as through the use of stainless steel, polymeric, or glass capillary tubes, laminated stencil layers, or by processing various materials using conventional processing techniques such as micromachining, etching or molding. The stationary phase material included in the columns 13A–13N may be selected to provide the desired performance characteristics. It will be readily understood by one skilled in the art that any form or configuration of HPLC columns may be used, the appropriate column, fabrication method and stationary phase material being selected to match the performance characteristics required for the particular separation(s).

The system 10 also includes valves 18A–18N (numbering for valves 18B–18E is omitted for clarity) interposed between each separation column 13A–13N and its respective storage line 16A–16N. A fluid/pressure source 20 connects to the valves 18A–18N. Preferably, the fluid/pressure source comprises a source of purge gas in at least intermittent fluid communication with the storage lines 16A–16N and adapted to discharge at least a portion of the contents of each storage line 16A–16N. Each of the storage lines 16A–16N connect to an associated electrospray needle 24A–24N (numbering for needles 24B–24E is omitted for clarity) and the positioning of the needles 24A–24N relative to the mass spectrometer 14 is controlled with a translation stage 22 (or equivalent fluid directing element), which may have two or more degrees of freedom. The mass spectrometer 14 may be any suitable MS device selected by one skilled in the art, including, but not limited to quadrupole, tandem, triple quadrupole, ion trap, or time-of-flight mass spectrometers. It will be readily apparent to one skilled in the art that, in addition to or as an alternative to mass spectrometers, other analytical tools may be used in conjunction with fluid handling systems according to the present invention.

In operation, the desired HPLC separations are performed simultaneously in columns 13A–13N. The output stream from each column 13A–13N is directed into its associated storage line 16A–16N. Referring to FIG. 7, it should be understood that the output stream 350 from an HPLC column includes a waste segment 352 and a species segment 354. The waste segment 352 comprises the mobile phase that is forced through the column to wet the stationary phase to prepare it for the separation operation. The species segment 354 comprises mobile phase combined with the sample, which, after passage through the column, has been separated into its component species 356A–356N. The waste segment 352 of the output stream may be discarded, as it typically contains no materials of interest.

Referring again to FIG. 3, the storage lines 16A–16N are filled simultaneously. A waste segment of the output stream may be discarded before entering the storage lines or may travel through the storage lines before being diverted to a waste collector (not shown). The volume of each storage line 16A–16N is preferably selected to accommodate the species segment of mobile phase output for a single chromatographic separation on its respective column 13A–13N. Thus, if the volume of the species segment of the mobile phase output of a separation is X microliters, the volume (V) of the storage line ($V=\pi(0.5 \times ID)^2 \times L$, where ID is the inner diameter of the storage line and L is the length of the storage line) should be greater than or equal to X microliters. For example, a species segment having a volume of about 0.003 fl. oz. (about 100 microliters) requires an associated storage line 16A–16N having a length of approximately twenty-five feet (about seven and six tenth meters), assuming the internal diameter of the storage line 16A–16N is approximately five mils (about 130 microns).

Because all the separations may be run simultaneously, once the separations are complete and the species segments are stored in the storage lines 16A–16N, the valves 18A–18N may be closed and the device 12 may be prepared for the next run while the stored species segments are analyzed. However, storing the species segments for long periods of time (e.g., many minutes) may be of concern as diffusion between the separated bands of analyte and the solvent may occur. Such diffusion could cause band broadening, thereby affecting the signal clarity of the sample as it is analyzed by the mass spectrometer. It has been found that maintaining microfluidic dimensions in the storage lines 16A–16N minimizes the size of the diffusion interface between bands and solvents, thereby mitigating band broadening. Moreover, it has been found that such diffusion produces a very small contribution to total band broadening compared to other features of the system (e.g., fluid interconnections, valves, frits, etc.). As a result, there is considerable flexibility in the size of capillary tubing required to produce sufficient system performance.

Another concern is the degree of band broadening caused by the travel of the eluate stream through the entire length of the storage line 16A–16N. Band broadening in this context may be characterized by a band broadening factor (BF), which equals the ratio of peak width after passing through a storage line ("final peak width" or $W_x$) to peak width measured at the injector ("injector peak width" or $W_o$), (i.e., $BF=W_x/W_o$). Thus, if a one minute peak traveling through a seven meter storage line were to broaden to two minutes, the band broadening factor would be two (BF=2 min./1 min.=2). Another method for characterizing the band broadening is to determine the absolute or additive broadening (AB) factor, which is equal to the difference between the final peak width minus the injector peak width (i.e., $AB=W_x-W_o$). While both measures are useful, it has been found that the band broadening caused by travel through storage lines appears to be fixed or constant and not linear or geometric. Thus, in a storage line where a one-minute band is broadened to two minutes upon exiting the line, a two-minute band also is like to broaden by one minute. Accordingly, the additive broadening factor may be a more desirable measure of storage line performance.

Referring to FIGS. 6A–6B, an experiment was conducted using a test system 300A, in which a reference analyte was provided from an injector 302A directly into an ultraviolet (UV) detector 304A. The same reference analyte was then introduced by an injector 302B into a storage line 306 and then to a UV detector 304B located at the terminus of the storage line 306. The reference analyte was a 0.5 microliter plug of caffeine (2 milligrams/milliliter) introduced into a solvent flowing at 5 microliters/min. Table 1 shows the results of a comparison between storage lines fabricated with polyetheretherketone (PEEK) and stainless steel. Both experiments were performed using twenty-five foot (7.6 meter) storage lines with inner diameters of five mils (130 microns). Table 2 show the results of a similar experiment comparing the performance of PEEK storage lines having inner diameters of five and seven mils (130 and 180 microns, respectively) and lengths of twenty five feet (7.6 meters) and thirteen feet (four meters), respectively.

TABLE 1

Comparison of PEEK and Stainless Steel Storage Lines

| Material | W(x) (min) | W(o) (min) | BF | AB (min) |
|---|---|---|---|---|
| PEEK (5 mil) | 0.393 | 0.118 | 3.33 | 0.275 |
| SS (5 mil) | 0.604 | 0.118 | 5.12 | 0.486 |

TABLE 2

Comparison of Different Inner Diameters of PEEK Storage Lines

| ID (mil) | W(x) (min) | W(o) (min) | BF | AB (min) |
|---|---|---|---|---|
| 5 | 0.393 | 0.118 | 3.33 | 0.275 |
| 7 | 0.684 | 0.118 | 5.80 | 0.566 |

These experiments demonstrate that band broadening may be controlled by selecting the size/geometry and material properties of the storage lines 16A–16N. Thus, band broadening may be minimized by reducing the interior diameter of the storage lines 16A–16N and/or using a more hydrophobic material, such as PEEK. These parameters may be varied to tailor the system to the desired results. For example, wider or larger diameter storage lines may be used to accelerate processing where band resolution is not critical. Likewise, where band resolution is paramount, very narrow or smaller diameter storage lines may be used to minimize diffusion and broadening. Also, other materials, such as, but not limited to, polytetrafluoro-ethylene (PTFE), may be selected to further minimize or otherwise manipulate the behavior of the output stream in the storage lines 16A–16N. Suitable materials will be readily apparent to one skilled in the art.

When the separation is complete and all of the storage lines 16A–16N are filled, the fluid flow to the storage lines 16A–16N from the separation columns 13A–13N is terminated. The flow may be terminated at the pressure source driving the separation (not shown) or by the actuation of the valves 18A–18N. The valves 18A–18N may then be selectively activated to direct pressurized fluid from fluid/pressure source 20 into each storage lines 16A–16N to drive the stored fluid into the mass spectrometer 14. The valves 18A–18N are preferably actuated sequentially, allowing the entire contents of each storage line 16A–16N to be analyzed by the mass spectrometer 14 before the next storage line 16A–16N is selected.

Each storage line 16A–16N may be coupled with a dedicated electrospray needle 24A–24N in order to deliver analyte from the storage line 16A–16N to the mass spectrometer 14. If desired, make-up fluid such as nebulizing gas may be additional supplied to the needles 24A–24N. The electrospray needles 24A–24N are preferably fabricated in a closely spaced array positioned in front of the mass spectrometer inlet orifice 26. When a particular output stream is to be analyzed, the needle 24A–24N corresponding to the selected storage line 16A–16N is positioned in front of the orifice 26 by the translation stage 22. The fluid flow is actuated at the upstream end of the storage line 16A–16N by actuating a valve 18A–18N to provide pressurized fluid from fluid/pressure source 20 to the storage line 16A–16N. To analyze another sample, the translation stage 22 is repositioned and the flow actuated for the next corresponding storage line 16A–16N. This interface has the advantage of fewer connections that could cause band broadening.

In an alternative embodiment, shown in FIG. 4, a system 110 is similar to the system 10 shown in FIG. 3 except that the storage lines 116A–116N are connected to the inputs of a multi-port switching rotary valve 130 (such as produced by Valco Instrument Co. Inc, "VICI," Houston, Tex.) or equivalent fluid directing element. The single output 132 of the rotary valve 130 is linked directly to the standard input interface of the mass spectrometer 114. The rotary valve 130 is actuated to the desired storage line 116A–116N to the mass spectrometer 114. A fluid/pressure source 120 preferably connects to the fluid directing elements 118A–118N upstream of the storage lines 116A–116N. Preferably, the fluid/pressure source 120 comprises a source of purge gas in at least intermittent fluid communication with the storage lines 116A–116N and adapted to discharge at least a portion of the contents of each storage line 116A–116N. The interface shown in FIG. 4 has the advantage of requiring little or no modification of existing ES/MS interfaces and, thus, would be readily adapted to almost any commercially available ES/MS. The rotary valve 132, however, may include a dead volume that could result in undesirable band broadening. Other multi-port valves (not shown), such as translational multi-port switching valves, also may be used.

In addition, any suitable interface between the storage lines and the mass spectrometer may be used. For example, with the benefit of the present disclosure, any of the sampling interfaces described in U.S. Pat. No. 6,410,915 to Bateman et al.; U.S. Pat. No. 6,191,418 to Hindsgaul et al.; U.S. Pat. No. 6,066,848 to Kassel et al.; and U.S. Pat. No. 5,872,010 to Karger et al. could be modified to provide a switching, rather than a sampling, function and thus used in conjunction with storage lines.

In another preferred embodiment, shown in FIG. 5, a HPLC/MS system 210 also may include a pre-screening sensor array 230 in communication with a detector 250. The pre-screening detector array 230 includes sensors 232A–232N and may sense any desirable or useful characteristic of the output of columns 213A–213N such as transmissive or reflective response to ultraviolet (UV) or visible light. The detector 250 may be used to analyze the sensor data, identify compounds or regions of interest in the output streams, and/or provide data to control the analysis of the output streams (e.g., by providing actuating signals to the fluid/pressure source 220 that connects to the valves 218A–218N). For example, if a chromatogram produced by the detector 250 indicates large separation of bands (i.e., good resolution) the mass spectrometer analysis may be performed more quickly (e.g., by purging the storage lines 216A–216N very quickly) without concerns of data loss. If, in contrast, a chromatogram produced by the detector 250 shows tightly spaced bands, the mass spectrometer analysis can be performed much more slowly in order to generate greater data resolution. To permit independent operation of the liquid phase separation and the subsequent mass spectrometric analysis, it is desirable to provide separate driving means for each. For example, a liquid chromatography subsystem is operated with one or more pumps (e.g., such as within the fluid supply system 614 shown in FIG. 9), with the pressure supplied by the pumps preferably being sufficient to drive eluate from the separation regions 213A–213N into the corresponding storage regions 216A–216N. Thereafter, a separate source of purge gas (e.g., source 220) is used to purge at least a portion of the contents of each storage region 216A–216N toward the inlet orifice 226 of the mass spectrometer 214. Also, the detector 250 may be used to identify the waste and species segments of the output stream to control the diversion of the stream to a waste collector.

A feedback system as described above may be used to vary the flow rate of a particular sample to provide high resolution during signal analysis and higher speed between signals. In other words, data from the detector 250 could be used to accelerate the flow from the storage lines 216A–216N via the orifice 226 into the mass spectrometer 214 between bands and decelerate the flow rate when the bands are being introduced into the mass spectrometer 214.

It may be desirable to position a sensor array 252 proximate to the interface between the storage lines 216A–216N and the mass spectrometer 214 to allow for more accurate control of the flow rate vis-à-vis the output stream characteristics. Alternatively, sensor arrays 230, 252 may be used at either end of the storage lines 216A–216N to provide even more control.

As indicated above, it may be desirable to control the flow rate of fluid from the storage lines 216A–216N to the mass spectrometer 214 to accomplish one or more desired results. For example, the output flow rate may be varied to optimize signal resolution as described above. Alternatively, the output flow rate may be accelerated for each storage line 216A–216N uniformly to accelerate overall processing times. In one embodiment, if six separation columns are used, the flow rate from the storage lines 216A–216N may be adjusted so that the time to output fluid from one of the storage lines 216A–216N into the mass spectrometer 214 has a duration of one sixth of the duration of the separation. In this manner, the entire output of all the columns 213A–213N may be analyzed in the time required to perform all of the separations.

Of course, the rate at which the samples are output from the storage lines 216A–216N may affect the quality of the data as a consequence of fluid flow effects on the samples (e.g., a high flow rate may induce turbulence thereby causing band widening or loss of resolution). Thus, it may be desirable to alter the flow rate in a manner more suited to the desired output resolution. For example, multiple mass spectrometers may be used to allow a slower output flow rate. In the embodiment described above, the use of two mass spectrometers would allow the output of the six storage lines 216A–216N two be divided into two sets of three. The mass spectrometry analysis could then be performed in the same amount of time, but only requiring increasing the output flow rate by a factor of three, rather than six. This approach may be used for any number of columns and flow rates. A device incorporating sixteen, twenty-four or more separation columns could be coupled with two, four, eight or more mass spectrometers to allow for the desired output flow rate, but still minimizing the total number of mass spectrometers required to perform the desired analysis. One skilled in the art will readily recognize that any and all of the approaches described above may be combined in any number of ways to achieve the desired system performance and data resolution.

In addition, output signals from the detector 250 may be used to control valves or equivalent fluid directing elements 218A–218N and re-direct a portion of each output flow stream through sample diversion lines 234 to a fraction collector 236. In this manner, discrete samples of interest may be collected and stored for other forms of analysis. Alternatively, or in addition, valves (fluid directing elements) 238A–238N or fluid flow splitters (not shown) may be positioned proximate to the interface between the storage lines 216A–216N in order to divert portions of the output streams through diversion lines 242 into a fraction collector 236. The sensor array 252 may be used to provide data to the detector 250 to control the operation of the valves 238A–238N.

If splitters are used to divert some eluate to a fraction collector, a representative portion of each eluate stream should still be supplied to the mass spectrometer 214 if it is desired to maintain an uninterrupted (i.e., lossless) data stream. In this manner, plots of data with respect to time can be constructed without requiring the undesirable interpolation inherent to conventional parallel sampling-type interfaces.

Storage systems according to the invention allow entire output streams to be isolated and stored for individual analysis. This approach has several advantages over real-time sampling systems, including the negation of the data loss, improved signal resolution and the ability to simultaneously perform the MS analysis while the separation columns are flushed and prepared for separation of subsequent samples. In addition, the rotary valve HPLC/MS coupling system eliminates the need to modify the ES/MS interface of existing ES/MS devices, thus allowing the system to be adapted to almost any commercially available ES/MS. The arrayed ES coupling method utilizes a much more limited range of motion. This, in combination with the ability to store the output streams for an extended period of time, allows the array to be positioned more easily and accurately than a rapidly cycling sampling system because the array is not required to move with immense speed. This increase in accuracy as well as the improvement of signal clarity and negation of data loss offsets the potential need to modify the ES/MS interface to accommodate the array.

Figure 8:
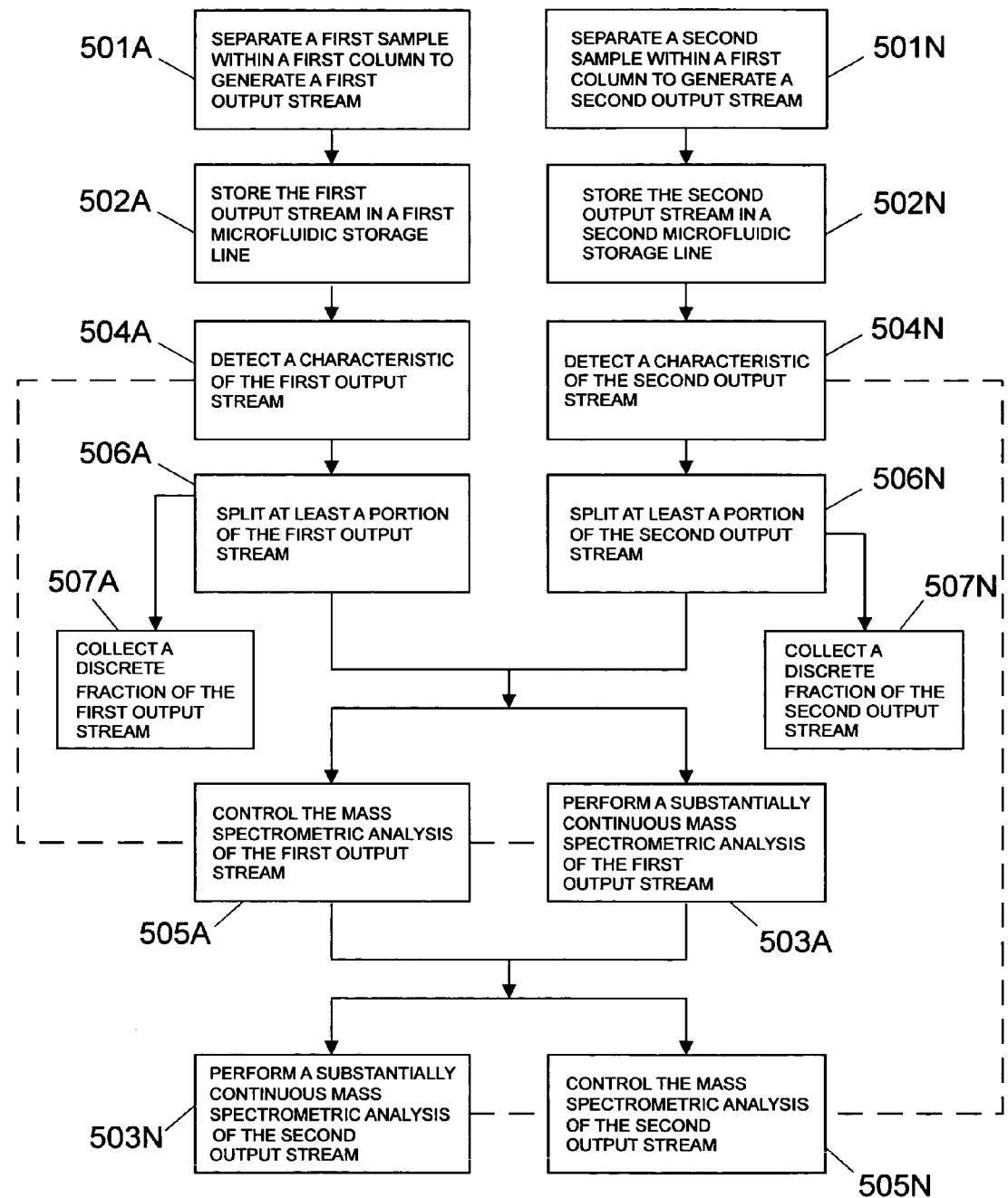
FIG. 8 is a flowchart of a method for operating a multi-column liquid chromatography apparatus with storage lines coupled to a mass spectrometer.

A flowchart outlining the steps of a method for operating a multi-column liquid chromatography apparatus with storage lines coupled to a mass spectrometer is provided in FIG. 8. A first step 501A includes separating the first sample within a first separation column to generate a first output stream. A second step 502A includes storing the first output stream in a first microfluidic storage line. A third step, 501N, which occurs substantially simultaneously to the first step 501A, includes separating a second sample within a second separation column to generate a second output stream. A fourth step 502N, which occurs substantially simultaneously to the second step 502A, includes storing the second output stream in a second microfluidic storage line. A fifth step 503A includes performing a substantially continuous mass spectrometric analysis of the contents of the first output stream. A sixth step, which occurs substantially simultaneously to the fifth step 503A, includes performing a substantially continuous mass spectrometric analysis of the contents of the second output stream. (Note that while FIG. 8 illustrates operation of a system with only two parallel sample separation columns and microfluidic storage lines, it will be readily understood by one skilled in the art that any number of columns and storage lines may be used.)

Optional steps include detecting a characteristic of the first and/or second output streams 504A, 504N and controlling the mass spectrometric analysis in accordance with the detected characteristics 505A, 505N (as described above). For example, the flow rate of the output streams into the mass spectrometer may be varied based on the presence or absence of species of interest. Optional steps also include splitting the output streams 506A, 506N so that a portion of each may be collected in a fraction collector 507A, 507N.

A wide variety of samples may be used with methods and systems according to the present invention. Preferably, any of the method steps may be automated. Automation means preferably include a programmable microprocessor such as contained within a personal computer or other conventional processing device.

HPLC/MS System with Parallel Eluate Storage Banks

Figure 9:
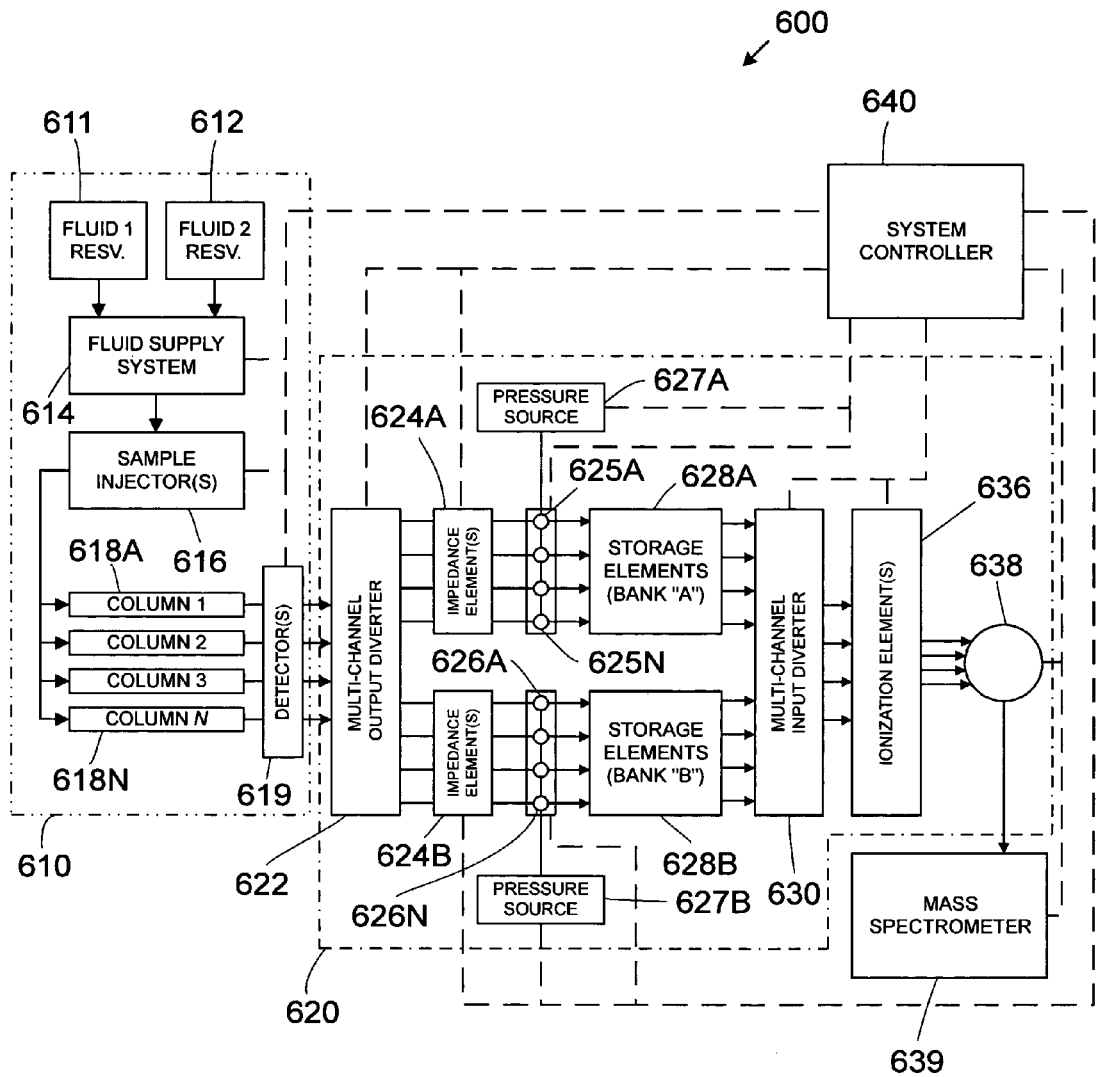
FIG. 9 is a schematic of a first integrated, multi-channel liquid chromatography/mass spectrometer analysis system, the system having switchable banks of high-capacity capillary storage elements disposed between a group of chromatography columns and the inlet of a mass spectrometer.

In one embodiment, a multi-column HPLC/MS system includes parallel banks of eluate storage regions. An improved HPLC/MS analytical system 600 having parallel eluate storage capability to promote increased analytical throughput is illustrated in FIG. 9. One advantage of providing parallel eluate storage capability is that a first bank of storage elements (e.g., storage elements 628A) can be filled with eluate from a group of separation columns (e.g., columns 618A–618N) while storage elements (e.g., elements 628B) from a second bank are sequentially discharged into a mass spectrometer (e.g., mass spectrometer 639) for mass analysis. If desired, additional banks of capillary storage lines may be provided, to permit execution of additional functions (e.g., rinsing or other preparatory steps) on such storage lines while the first and second banks of capillary storage lines are being filled and discharged, respectively.

The system 600 includes an HPLC subsystem 610 and a MS interface subsystem 620 each in communication with a system controller 640. The HPLC subsystem 610 includes two fluid reservoirs 611, 612, such as may contain typical HPLC-grade solvents including liquids such as purified water, acetonitrile, methanol, isopropyl alcohol, or dimethylsulfoxide. A fluid supply system 614 (typically including multiple HPLC pumps) supplies solvents from the reservoirs 611, 612 to multiple separation columns 618A, 618N. Preferably, a mixer and splitting network (not shown) is disposed between the fluid supply system 614 and the columns 618A–618N. One or more sample injectors 616 (e.g., conventional loop-type sample injection valves or on-column sample injection means such as including the sample injection ports 428A–428N provided in the multi-column HPLC device 400 described previously) may be provided between the fluid supply system 614 and the HPLC columns 618A–618N. Following separation of sample in the columns 618A–618N, the resulting eluate flows through one or more suitable detectors (e.g., UV-Vis, fluorescent, or equivalent flow-through detector types) to the MS interface subsystem 620.

The MS interface subsystem 620 includes two parallel banks of storage elements 628A, 628B each preferably containing multiple capillary storage lines, with at least one storage line in each bank 628A, 628B associated with each column 618A–618N. In one embodiment, each individual storage line has sufficient volumetric capacity to store all the eluate of interest from an entire separation run performed in its corresponding separation column. Switching between the banks of parallel eluate storage elements 628A, 628B is provided by way of an upstream multi-channel output diverter (or similar fluid directing element) 622 and a multi-channel input diverter (or similar fluid directing element) 630. Each diverter 622, 630, which is preferably microfluidic to reduce band broadening, may include multiple discrete switching elements (e.g., multiple discrete valves, preferably valves with minimal dead volume) or may have the switching functions for multiple columns integrated into a single commonly-actuated multi-channel diverter device. Each individual storage element in the two storage banks 628A, 628B has an associated impedance element 624A, 624B and an individually actuatable purge initiation valve 625A–25N, 626A–626N, respectively. Each purge initiation valve 625A–625N, 626A–626N is in fluid communication with a pressure source 627A, 627B, preferably a source of pressurized relatively inert purge gas. The function of the purge initiation valves 625A–625N, 626A–626N is to periodically purge eluate from the storage lines into the mass spectrometer 639, with the impedance elements 624A–624N serving to prevent backflow of eluate or purge gas into the separation columns 618A–618N. As noted previously, each pressure source 627A–627B is preferably independent of the fluid supply system 614 associated with the chromatography subsystem 610 to permit eluate to be supplied to the mass spectrometer 639 at any desired flow rate independent of the separation process.

The impedance elements 624A–624N may include actuated valves, passive check valves, or simply high impedance media such as microporous materials. Each storage element within the banks 628A, 628B may further include eluate retention means such as a microbore septum or actuated valve (not shown) immediately downstream of the storage element to retain eluate before it is purged through action of the purge initiation valves 625A–625N. The downstream multi-channel input diverter 630 is in selective fluid communication with each bank of upstream storage elements 628A, 628B and is in constant fluid communication with the ionization element(s) 636 disposed downstream. While any of the various ionization types mentioned herein may be used, a preferred ionization means is electrospray ionization. An energy source (not shown) such as a voltage source (to provide electric ionization potential) with a source of heated gas (to promote evaporation of the solvent portion of the eluate) is preferably associated with the ionization element (s) 636. A multi-port switching valve 638 such as a rotary valve with a (e.g., low speed) rotating inlet aperture may be disposed downstream of the ionization element(s) 636 if multiple ionization elements (such as multiple electrospray needles, one associated with each column 618A–618N) are provided and immediately upstream of the inlet to a mass spectrometer 639. Alternatively, a translation stage or collection manifold (not shown) may be disposed between the input diverter 630 and a single ionization element 636 to eliminate with the need for a switching valve 638.

In operation of the system 600, the HPLC columns 618–618N and mass spectrometer 639 may operate on a substantially continuous basis. While the contents of the storage elements from a first bank (e.g., storage bank 628A) are being sequentially ionized, purged, and directed into the MS, the storage elements of a second bank may be receiving eluate from the HPLC columns 618A–618N, and vice-versa. In one embodiment, an additional diverter (not shown) may be provided immediately downstream of the columns 618A–618N to divert undesirable portions of the eluate streams to waste. The system controller 640 is preferably microprocessor-based and includes both hardware and software components to receive control inputs and permit execution of user-defined instruction sets. The controller 640 may include multiple discrete control elements including industrial controllers, personal computers, or similar control components, which may advantageously be networked or otherwise connected to permit communication between control components.

It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention and that the scope of the invention should be interpreted with respect to the following claims.

What is claimed is:

1. A system for analyzing a plurality of samples in parallel, the system comprising:
   a plurality of liquid phase separation regions;
   a first plurality of microfluidic storage regions;
   a second plurality of microfluidic storage regions;
   a first flow diverter disposed downstream of the plurality of liquid phase separation regions and disposed upstream of both the first plurality of storage regions and the second plurality of storage regions;
   a plurality of ionization sources disposed downstream of the first plurality of storage regions and the second plurality of storage regions; and a common mass spectrometer in at least intermittent fluid communication with each ionization source of the plurality of ionization sources.

2. The system of claim 1 wherein:
each liquid phase separation region of the plurality of liquid phase separation regions is adapted to separate a different sample of the plurality of samples in parallel, with each liquid phase separation region yielding an output stream having a species segment; and
each storage region of the first bank of storage regions and the second bank of storage regions has a volume sufficient to store substantially all of a species segment.

3. The system of claim 1 wherein each storage region of the plurality of first storage regions and the plurality of second storage regions comprises a capillary tube.

4. The system of claim 1 wherein each ionization source of the plurality of ionization sources is independently controlled.

5. The system of claim 1 wherein each liquid phase separation region of the plurality of liquid phase separation regions comprises a chromatographic separation column.

6. The system of claim 5 wherein each liquid phase separation region of the plurality of liquid phase separation regions comprises packed particulate stationary phase material.

7. The system of claim 1 wherein each liquid phase separation region of the plurality of liquid phase separation regions is disposed within a common body structure.

8. The system of claim 7 wherein each liquid phase separation region is microfluidic.

9. The system of claim 1, further comprising a flow-through detector disposed between the plurality of liquid phase separation regions and the mass spectrometer.

10. The system of claim 1, further comprising a common source of pressurized mobile phase in fluid communication with each liquid phase separation region of the plurality of liquid phase separation regions.

11. The system of claim 1, further comprising a source of purge gas in intermittent fluid communication with each storage region of the first plurality of storage regions and the second plurality of storage regions.

12. The system of claim 11, further comprising a flow-through detector, wherein operation of the source of purge gas is responsive to the flow-through detector.

13. The system of claim 1, further comprising a translation stage disposed between and adapted to permit fluid communication between any storage region of the first plurality of storage regions and the mass spectrometer, and between any storage region of the second plurality of storage regions and the mass spectrometer.

14. The system of claim 1, further comprising:
a fraction collector; and
a plurality of flow splitters, each flow splitter of the plurality of flow splitters being in at least intermittent fluid communication with the fraction collector and being associated with a different separation region of the plurality of separation regions.

15. A system for analyzing a plurality of samples in parallel, the system comprising:
a plurality of liquid phase separation regions;
a first bank of microfluidic storage regions;
a second bank of microfluidic storage regions;
a first fluid directing element permitting switchable fluid communication between the plurality of liquid phase separation regions and the first bank of storage regions, and between the plurality of liquid phase separation regions and the second bank of storage regions;
a common mass spectrometer; and
a second fluid directing element permitting switchable fluid communication between the first bank of storage regions and the mass spectrometer, and between the second bank of storage regions and the mass spectrometer.

16. The system of claim 15 wherein:
each liquid phase separation region of the plurality of liquid phase separation regions is adapted to separate a different sample of the plurality of samples in parallel, with each liquid phase separation region yielding an output stream having a species segment; and
each storage region of the first bank of storage regions and the second bank of storage regions has a volume sufficient to store substantially all of a species segment.

17. The system of claim 15 wherein each storage region of the first bank of storage regions and the second bank of storage regions comprises a capillary tube.

18. The system of claim 15, further comprising a plurality of ionization sources disposed between the second fluid directing element and the common mass spectrometer.

19. The system of claim 18 wherein each ionization source of the plurality of ionization sources is independently controlled.

20. The system of claim 15 wherein each liquid phase separation region of the plurality of liquid phase separation regions comprises a chromatographic separation column.

21. The system of claim 20 wherein each liquid phase separation region of the plurality of liquid phase separation regions comprises packed particulate stationary phase material.

22. The system of claim 15 wherein each liquid phase separation region of the plurality of liquid phase separation regions is disposed within a common body structure.

23. The system of claim 15 wherein each liquid phase separation region of the plurality of liquid phase separation regions is microfluidic.

24. The system of claim 15, further comprising a flow-through detector disposed downstream of a storage region of any of the first bank and the second bank of storage regions.

25. The system of claim 15, further comprising a common source of mobile phase in fluid communication with each liquid phase separation region of the plurality of liquid phase separation regions.

26. The system of claim 15, further comprising a source of purge gas in intermittent fluid communication with a storage region of any of the first bank and the second bank of storage regions.

27. The system of claim 26, further comprising a flow-through detector, wherein operation of the source of purge gas is responsive to the flow-through detector.

28. The system of claim 15 wherein the second fluid directing element comprises a translation stage adapted to permit fluid communication between any storage region of the first bank or second bank of microfluidic storage regions and the mass spectrometer.

29. A method for high throughput sample analysis employing a first liquid phase separation region, a second liquid phase separation region, a first microfluidic storage region in fluid communication with the first separation region, a second microfluidic storage region in fluid communication with the second separation region, a common mass spectrometer disposed downstream of the first storage region and the second storage region, and a source of purge gas in selectable fluid communication with the first storage region and the second storage region, the method comprising the steps of:

separating a first sample in first separation region to generate a first output stream storing the first output stream in the first microfluidic storage region;

purging, ionizing, and directing to a mass spectrometer at least a representative portion of the contents of the first each storage region;

substantially simultaneously with the purging, ionizing, and directing step, separating a second sample within the second separation region to generate a second output stream and storing the second output stream in the second microfluidic storage region.

30. A system for analyzing a first sample and a second sample in parallel, the system comprising:

a common mobile phase source;

a first liquid phase separation column in fluid communication with the mobile phase source and adapted to separate the first sample to generate a first output stream having a species segment;

a second liquid phase separation column in fluid communication with the mobile phase source and adapted to separate the first sample to generate a second output stream having a species segment;

a first microfluidic storage region in fluid communication with the first separation region;

a second microfluidic storage region in fluid communication with the second separation region;

a common mass spectrometer disposed downstream of the first storage region and the second storage region; and a source of purge gas in selectable fluid communication with the first storage region and the second storage region, the source of purge gas being adapted to sequentially discharge at least a portion of the contents of the first storage region and at least a portion of the contents of the second storage region into the mass spectrometer.

31. The system of claim 30, further comprising:

a first ionization source disposed between the first storage region and the mass spectrometer; and a second ionization source disposed between the second storage region and the mass spectrometer.

32. The system of claim 30, further comprising a flow-through detector, wherein operation of the source of purge gas is responsive to the flow-through detector.

* * * * *

UNITED STATES PATENT AND TRADEMARK OFFICE
CERTIFICATE OF CORRECTION

PATENT NO. : 7,214,320 B1
APPLICATION NO. : 10/979946
DATED : May 8, 2007
INVENTOR(S) : Gregori et al.

Page 1 of 1

It is certified that error appears in the above-identified patent and that said Letters Patent is hereby corrected as shown below:

On the second Title page item (56),

Page 2, Column 1, FOREIGN PATENT DOCUMENTS, first entry: "WO-9809315" should be -- WO-98/09315 --

Page 2, Column 1, OTHER PUBLICATIONS, first entry, third line: "waters Micromass" should be -- Waters Micromass --

Page 2, Column 2, OTHER PUBLICATIONS, third entry, first line: "Little, David, et al., A prallel LC-MS/MS system" should be -- Little, David, et al., A parallel LC-MS/MS system --

Page 2, Column 2, OTHER PUBLICATIONS, sixth entry, first line: "Multi-Paraellel HPLC" should be -- Multi-Parallel HPLC --

Column 23, line 1: "separating a first sample in first" should be -- separating a first sample in the first --

Column 23, line 6: "each storage region" should be -- storage region --

Signed and Sealed this

Sixteenth Day of October, 2007

JON W. DUDAS
*Director of the United States Patent and Trademark Office*